(12) United States Patent
Spormann et al.

(10) Patent No.: US 8,063,192 B2
(45) Date of Patent: Nov. 22, 2011

(54) MICROBIAL REDUCTIVE DEHALOGENATION OF VINYL CHLORIDE

(75) Inventors: Alfred M. Spormann, Stanford, CA (US); Jochen A. Müller, Baltimore, MD (US); Bettina M. Rosner, Berlin, DE (US); Gregory Von Abendroth, Nannhein, DE (US); Galit Meshulam-Simon, Los Altos, CA (US); Perry L McCarty, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 540 days.

(21) Appl. No.: 11/659,064

(22) PCT Filed: Aug. 2, 2005

(86) PCT No.: PCT/US2005/027565
§ 371 (c)(1),
(2), (4) Date: Mar. 11, 2009

(87) PCT Pub. No.: WO2006/017576
PCT Pub. Date: Feb. 16, 2006

(65) Prior Publication Data
US 2009/0176210 A1    Jul. 9, 2009

Related U.S. Application Data

(60) Provisional application No. 60/598,459, filed on Aug. 2, 2004.

(51) Int. Cl.
C07H 21/04    (2006.01)
(52) U.S. Cl. .................. 536/23.7; 536/24.32; 536/24.33
(58) Field of Classification Search .................. None
See application file for complete search history.

(56) References Cited

U.S. PATENT DOCUMENTS 7,115,734 B2 * 10/2006 Nakamura et al. ............ 536/24.3
7,618,814 B2 * 11/2009 Bentwich .................... 435/320.1
2006/0057564 A1 *  3/2006 Wang ................................ 435/6

OTHER PUBLICATIONS

Skolnick et al. Trends in Biotechnology 18: 34-39, 2000.*
Cupples; et al., "Growth of a Dehalococcoides-Like Microorganism on Vinyl Chloride and cis-Dichloroethene as Electron Acceptors as Determined by Competitive PCR", Applied and Environmental Microbiology (2003), 69 (2):953-959.
He; et al., "Complete Detoxification of Vinyl Chloride by an Anaerobic Enrichment Culture and Identification of the Reductively Dechlorinating Population as a Dehaloccoides Species", Applied and Environmental Microbiology (2003), 69(2):996-1003.
He; et al., "Detoxification of vinyl chloride to ethene coupled to growth of an anaerobic bacterium", Nature (2003), 424:62-65.
Hendrickson; et al., "Molecular Analysis of Dehalococcoides 16S Ribosomal DNA from Chloroethene-Contaminated Sites throughout North America and Europe", Applied and Environmental Microbiology (2002), 68 (2):485-495.
Magnuson; et al., "Reductive Dechlorination of Tetrachloroethene to Ethene by a Two-Component Enzyme Pathway", Applied and Environmental Microbiology (1998), 64(4):1270-1275.
Magnuson; et al., "Trichloroethene Reductive Dehalogenase from *Dehalococcoides ethenogenes*: Sequence of tceA and Substrate Range Characterization", Applied and Environmental Microbiology (2000), 66(12):5141-5147.
Maymo-Gatell; et al., "Isolation of a Bacterium that Reductively Dechlorinates Tetrachloroethene to Ethene", Science (1997), 276:1568-1571.
Maymo-Gatell; et al., "Reductive Dechlorination of Chlorinated Ethenes and 1,2-Dichloroethane by "*Dehalococcoides ethenogenes*"195", Applied and Environmental Microbiology (1999), 65(7):3108-3113.
Maymo-Gatell; et al., "Reductive Dechlorination of cis-1,2-Dichloroethene and Vinyl Chloride by "*Dehalococcoides ethenogens*"", Environmental Science & Technology (2001), 35(3):516-521.
Rosner; et al., "In Vitro Studies on Reductive Vinyl Chloride Dehalogenation by an Anaerobic Mixed Culture", Applied and Environmental Microbiology (1997), 63(11):4139-4144.

* cited by examiner

*Primary Examiner* — S. Devi
(74) *Attorney, Agent, or Firm* — Bozicevic, Field & Francis LLP; Pamela J. Sherwood

(57) ABSTRACT

Compositions and methods are provided that relate to the bioremediation of chlorinated ethenes, particularly the bioremediation of vinyl chloride by *Dehalococcoides*-like organisms. An isolated strain of bacteria, *Dehalococcoides* sp. strain VS, that metabolizes vinyl chloride is provided; the genetic sequence of the enzyme responsible for vinyl chloride dehalogenation; methods of assessing the capability of endogenous organisms at an environmental site to metabolize vinyl chloride; and a method of using the strains of the invention for bioremediation.

4 Claims, 11 Drawing Sheets

FIGURE 3

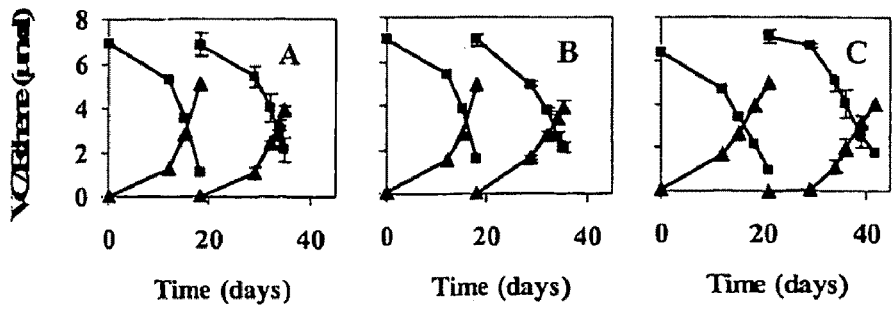

FIGURE 6  VC (squares) and ethene (triangles) by Victoria (A), KB-1/VC (B) and Pinellas (C) cultures. Following the formation of 5 μmol of ethene (day 18 for A and B, day 21 for C), culture (200 μL) was transferred to triplicate media bottles and VC was added (200 μL), with the results shown. Error bars, following these transfers, represent standard deviations for triplicate samples. Lines do not represent model simulations.

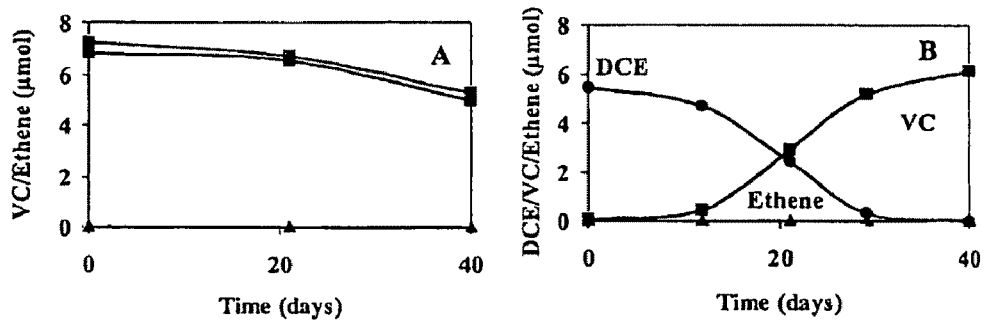

FIGURE 7  DCE (circles), VC (squares) and ethene (triangles) mass change with time in *D. ethenogenes* strain 195 cultures. Cultures were supplied with either VC (A) or DCE (B). Lines do not represent model simulations.

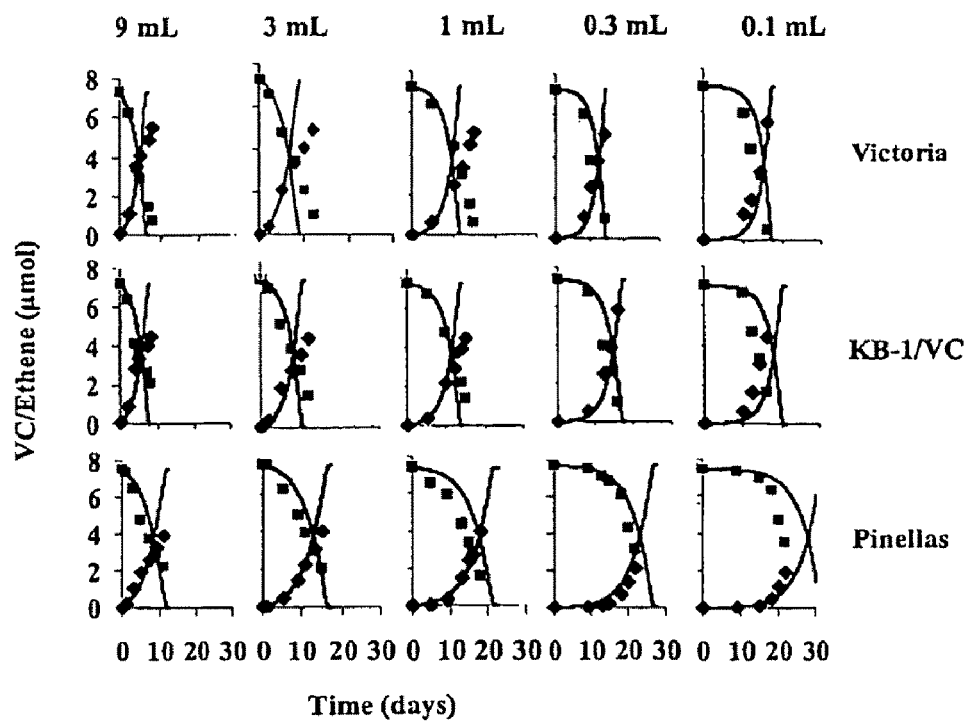
FIGURE 8  VC (squares) and ethene (diamonds) by Victoria, KB-1/VC and Pinellas cultures inoculated with 9, 3, 1, 0.3 or 0.1 mL of culture. Lines represent model simulations as discussed in the text.

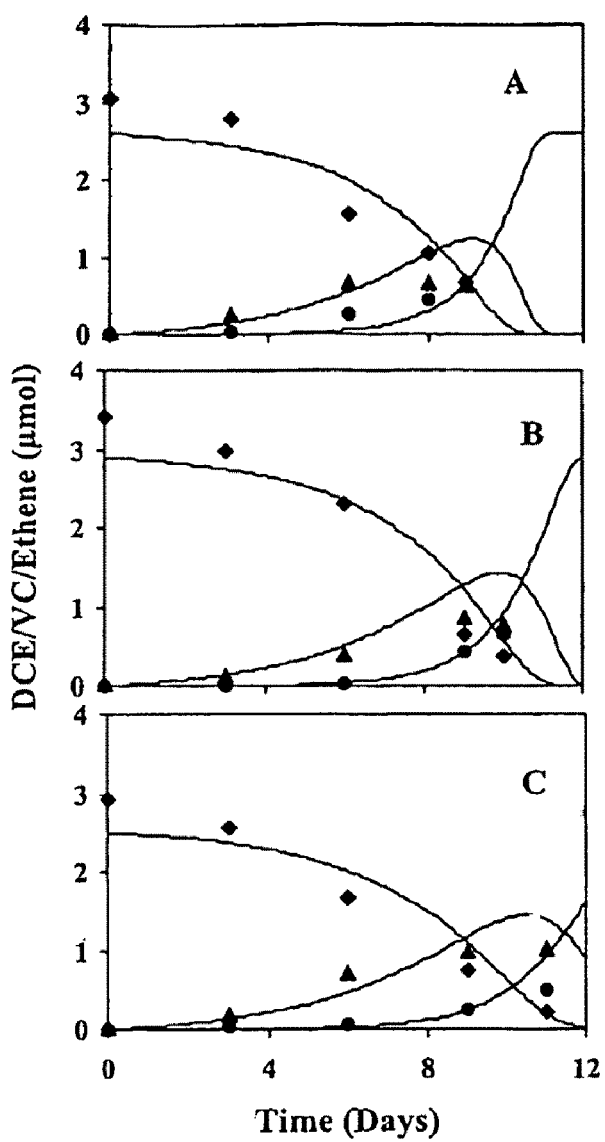
FIGURE 9  Reductive dehalogenation of DCE to ethene by (A) Victoria culture, (B) KB-1/VC culture, and (C) Pinellas culture. Symbols represent DCE (diamonds), VC (triangles), and ethene (circles). Lines represent model simulations as discussed in the text.

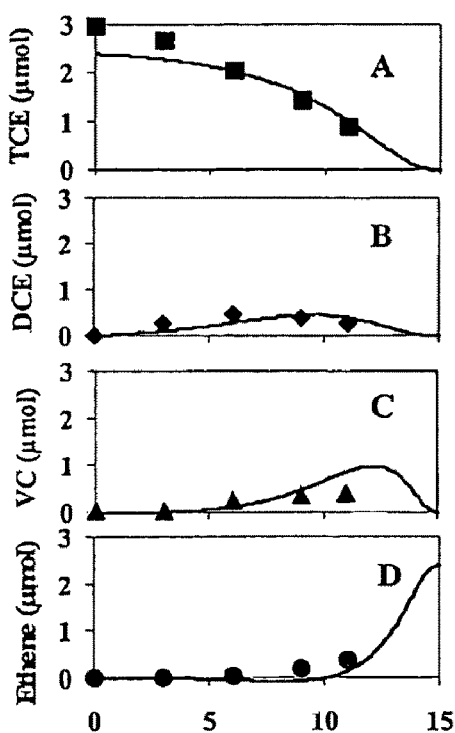
FIGURE 10  Reductive dehalogenation of TCE to ethene by the Pinellas culture. Symbols represent TCE (squares), DCE (diamonds), VC (triangles), and ethene (circles). Lines represent model simulations as discussed in the text.

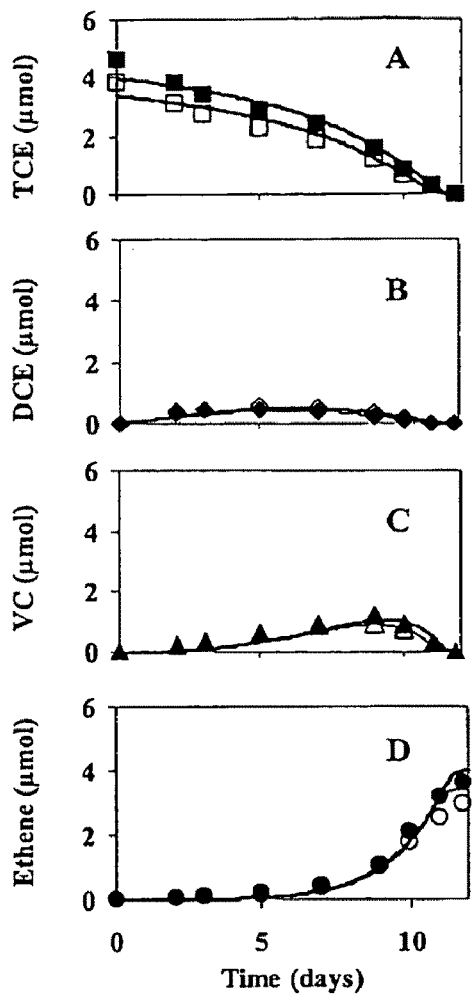
FIGURE 11  TCE (A), DCE (B), VC (C) dechlorination and ethene formation (D) in duplicates of the VC enrichment of strain VS from the Victoria culture. Lines represent model simulations, as discussed in the text.

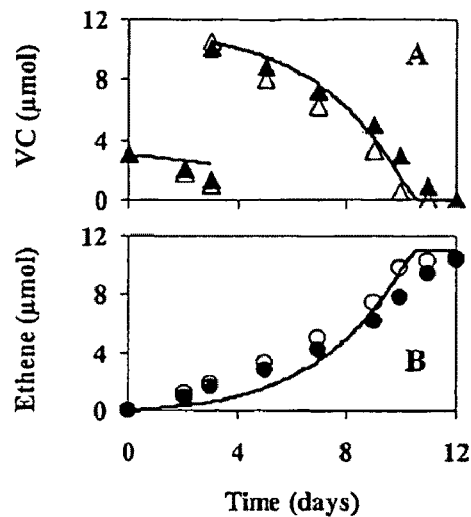
FIGURE 12. VC dechlorination (A) and ethene formation (B) in duplicates of the VC enrichment of strain VS. Lines represent model simulations, as discussed in the text.
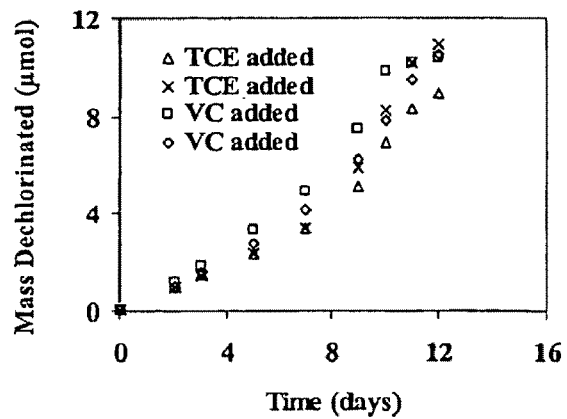
FIGURE 13. Comparison of mass dechlorinated (μmol chloride produced) with time by the VC enrichment of strain VS supplied with either TCE (triangles and crosses) or VC (squares and diamonds).

SEQUENCE LISTING

```
<160> NUMBER OF SEQ ID NOS: 44

<210> SEQ ID NO 1
<211> LENGTH: 2794
<212> TYPE: DNA
<213> ORGANISM: Dehalococcoides sp. VS
<220> FEATURE:
<221> NAME/KEY: CDS
<222> LOCATION: (623)...(2182)
<220> FEATURE:
<221> NAME/KEY: CDS
<222> LOCATION: (2223)...(2504)

<400> SEQUENCE: 1
aattactggg tgtacctgac tatgacgcgg ctcaagaagc cgggaatctt attcttaacc    60
tgtcatcgct ctggtccaag gccaacttat cagagcagaa aaagatactc cttaccacgc   120
tggacggggt ctatgtggat gtgaaagagc atcgctcggt aatagcagtt aaagccaagc   180 caccttcag gcctatcttt caggtggcag tttcaaagaa agaatctaag attcatattt     240
taaacgagcc attaagtcat gaacctagcg gctcgtccgt gtttctggtg gagacggggg   300
agggttggac tctccctgaa acaatggtga tggggtttgc aggatgttaa gatgcaaaaa   360
taactgtagt ttttattatt taaagtaact cgtgttcgat atgtagtaaa ttagcaaaga   420
ctagtactta agtattaata cttaagtaca tttattttat atatctttgc gtattttgtg   480
caattgacat tactatataa aatgctagaa tacaaataat caactgtgta tttgtactga   540
ggaaacgctt atggatattt ggcgttcagg aaagactgaa tggctctagg gaaagaccta   600
aatatatctt taggataaat tt atg agt aaa ttt cat aaa acg att agc cgc   652
                        Met Ser Lys Phe His Lys Thr Ile Ser Arg
                          1               5                  10 cga gat ttc atg aaa gga cta gga tta gcc ggg gca ggc ata ggc gct   700
Arg Asp Phe Met Lys Gly Leu Gly Leu Ala Gly Ala Gly Ile Gly Ala
             15                  20                  25 gtt gcg gcg tca gct ccg gtt ttt cat gac att gat gaa ctt gtt tca   748
Val Ala Ala Ser Ala Pro Val Phe His Asp Ile Asp Glu Leu Val Ser
         30                  35                  40 agc gaa gca aat tct act aaa gat caa cct tgg tac gtt aag cat cga   796
Ser Glu Ala Asn Ser Thr Lys Asp Gln Pro Trp Tyr Val Lys His Arg
     45                  50                  55 gag cat ttt gac cct acg att aca gtt gac tgg gat att ttt gat aga   844
Glu His Phe Asp Pro Thr Ile Thr Val Asp Trp Asp Ile Phe Asp Arg
 60                  65                  70 tat gac ggg tat cag cat aag ggt gtc tat gaa ggc cct cca gat gct   892
Tyr Asp Gly Tyr Gln His Lys Gly Val Tyr Glu Gly Pro Pro Asp Ala
 75                  80                  85                  90 ccc ttt aca tca tgg ggc aat agg ctt cag gtg aga atg tca ggt gaa   940
Pro Phe Thr Ser Trp Gly Asn Arg Leu Gln Val Arg Met Ser Gly Glu
                 95                 100                 105 gag caa aag aag cga att ttg gcc gct aaa aaa gag agg ttc cct ggt   988
Glu Gln Lys Lys Arg Ile Leu Ala Ala Lys Lys Glu Arg Phe Pro Gly
             110                 115                 120
```

| | |
|---|---|
| tgg gac ggt ggg tta cac ggg aga ggg gat cag cgg gcg gat gca cta<br>Trp Asp Gly Gly Leu His Gly Arg Gly Asp Gln Arg Ala Asp Ala Leu<br>             125                       130                       135 | 1036 |
| ttt tac gca gta act caa cca ttt cct ggt agt ggt gag gaa ggg cac<br>Phe Tyr Ala Val Thr Gln Pro Phe Pro Gly Ser Gly Glu Glu Gly His<br>140                       145                       150 | 1084 |
| gga cta ttc caa cct tat cct gat caa ccc ggt aag ttt tac gcg aga<br>Gly Leu Phe Gln Pro Tyr Pro Asp Gln Pro Gly Lys Phe Tyr Ala Arg<br>155                       160                       165                       170 | 1132 |
| tgg ggt ttg tat ggt ccg cca cat gat tca gcg cca cct gat ggg agc<br>Trp Gly Leu Tyr Gly Pro Pro His Asp Ser Ala Pro Pro Asp Gly Ser<br>             175                       180                       185 | 1180 |
| gta cca aaa tgg gag ggt act cca gaa gac aat ttt cta atg ctg agg<br>Val Pro Lys Trp Glu Gly Thr Pro Glu Asp Asn Phe Leu Met Leu Arg<br>190                       195                       200 | 1228 |
| gca gct gca aaa tat ttt ggt gct ggt ggc gtt ggt gct ctt aac ctg<br>Ala Ala Ala Lys Tyr Phe Gly Ala Gly Gly Val Gly Ala Leu Asn Leu<br>205                       210                       215 | 1276 |
| gca gat ccc aaa tgc aaa aaa cta ata tat aag aaa gct cag ccg atg<br>Ala Asp Pro Lys Cys Lys Lys Leu Ile Tyr Lys Lys Ala Gln Pro Met<br>220                       225                       230 | 1324 |
| act cta gga aaa gga aca tac agt gaa ata ggt gga cca gga atg atc<br>Thr Leu Gly Lys Gly Thr Tyr Ser Glu Ile Gly Gly Pro Gly Met Ile<br>235                       240                       245                       250 | 1372 |
| gat gca aaa att tat ccc aag gtt cct gac cat gcc gta cct att aac<br>Asp Ala Lys Ile Tyr Pro Lys Val Pro Asp His Ala Val Pro Ile Asn<br>                       255                       260                       265 | 1420 |
| ttt aag gaa gcg gat tat agc tac tac aat gat gca gag tgg gtt att<br>Phe Lys Glu Ala Asp Tyr Ser Tyr Tyr Asn Asp Ala Glu Trp Val Ile<br>                   270                       275                       280 | 1468 |
| cca aca aag tgt gaa tcc att ttc act ttc acc cta cct caa cca caa<br>Pro Thr Lys Cys Glu Ser Ile Phe Thr Phe Thr Leu Pro Gln Pro Gln<br>             285                       290                       295 | 1516 |
| gaa ctc aat aag agg acg ggt ggt ata gca ggt gct gga tca tat act<br>Glu Leu Asn Lys Arg Thr Gly Gly Ile Ala Gly Ala Gly Ser Tyr Thr<br>300                       305                       310 | 1564 |
| gta tac aaa gat ttc gct agg gta ggc act tta gtc caa atg ttt att<br>Val Tyr Lys Asp Phe Ala Arg Val Gly Thr Leu Val Gln Met Phe Ile<br>315                       320                       325                       330 | 1612 |
| aag tat cta ggt tat cac gct tta tat tgg cca att gga tgg gga ccg<br>Lys Tyr Leu Gly Tyr His Ala Leu Tyr Trp Pro Ile Gly Trp Gly Pro<br>                   335                       340                       345 | 1660 |
| ggt ggt tgc ttt acc act ttt gac ggg caa ggt gaa cag ggt aga aca<br>Gly Gly Cys Phe Thr Thr Phe Asp Gly Gln Gly Glu Gln Gly Arg Thr<br>                   350                       355                       360 | 1708 |
| ggt gct gct atc cat tgg aag ttt ggt tct tca caa cgt ggt tct gaa<br>Gly Ala Ala Ile His Trp Lys Phe Gly Ser Ser Gln Arg Gly Ser Glu<br>             365                       370                       375 | 1756 |
| aga gta ata act gat tta ccg ata gct cct acc ccg cca att gat gca<br>Arg Val Ile Thr Asp Leu Pro Ile Ala Pro Thr Pro Pro Ile Asp Ala<br>380                       385                       390 | 1804 |
| ggt atg ttt gag ttt tgc aaa acc tgt tat ata tgc cgt gac gtt tgc<br>Gly Met Phe Glu Phe Cys Lys Thr Cys Tyr Ile Cys Arg Asp Val Cys<br>395                       400                       405                       410 | 1852 |
| gtc tct ggg ggt gtg cac caa gaa gac gaa cca act tgg gat tca ggt<br>Val Ser Gly Gly Val His Gln Glu Asp Glu Pro Thr Trp Asp Ser Gly<br>                   415                       420                       425 | 1900 |
| aat tgg tgg aat gta caa gga tat ctc ggc tac cga acg gat tgg agt<br>Asn Trp Trp Asn Val Gln Gly Tyr Leu Gly Tyr Arg Thr Asp Trp Ser<br>                   430                       435                       440 | 1948 |

-continued

| | | |
|---|---|---|
| ggt tgc cat aac cag tgc ggt atg tgt caa tcc tcc tgc cct ttt act<br>Gly Cys His Asn Gln Cys Gly Met Cys Gln Ser Ser Cys Pro Phe Thr<br>               445                       450                       455 | 1996 |

```
ggt tgc cat aac cag tgc ggt atg tgt caa tcc tcc tgc cct ttt act    1996
Gly Cys His Asn Gln Cys Gly Met Cys Gln Ser Ser Cys Pro Phe Thr
            445                 450                 455 tat tta ggt ttg gaa aat gct tca tta gtg cac aaa ata gta aaa ggt    2044
Tyr Leu Gly Leu Glu Asn Ala Ser Leu Val His Lys Ile Val Lys Gly
        460                 465                 470 gtt gtt gct aac acg act gtt ttt aat agt ttt ttt acc aat atg gag    2092
Val Val Ala Asn Thr Thr Val Phe Asn Ser Phe Phe Thr Asn Met Glu
475                 480                 485                 490 aaa gca tta gga tat ggt gat tta acc atg gaa aat tct aac tgg tgg    2140
Lys Ala Leu Gly Tyr Gly Asp Leu Thr Met Glu Asn Ser Asn Trp Trp
                495                 500                 505 aaa gaa gaa gga ccg ata tac ggc ttt gat ccc ggt act tag            2182
Lys Glu Glu Gly Pro Ile Tyr Gly Phe Asp Pro Gly Thr
            510                 515 aaatagatac taaattcgat agaaaataaa ggaaattgaa atg gat gct ata tat    2237
                                            Met Asp Ala Ile Tyr
                                                            520 ttt ttc tta aca att gca tta gca gtt gga cta act atg cta ttt acc    2285
Phe Phe Leu Thr Ile Ala Leu Ala Val Gly Leu Thr Met Leu Phe Thr
525                 530                 535                 540 tgg ttt aaa aag aat aat atc act tta aag tgg aat gag tgg gta ctt    2333
Trp Phe Lys Lys Asn Asn Ile Thr Leu Lys Trp Asn Glu Trp Val Leu
                545                 550                 555 ggc ata ttg ggg ctg tta cta gct ttg ttt gct att caa cac aca tat    2381
Gly Ile Leu Gly Leu Leu Leu Ala Leu Phe Ala Ile Gln His Thr Tyr
            560                 565                 570 gcc agt gct aca tat gaa ttt gaa tat acg tca gca tgg ata gtg ggc    2429
Ala Ser Ala Thr Tyr Glu Phe Glu Tyr Thr Ser Ala Trp Ile Val Gly
        575                 580                 585 gtc ata gtg tta ttg tta gct gta gta ccg ttg tta ttt gcg gca aga    2477
Val Ile Val Leu Leu Leu Ala Val Val Pro Leu Leu Phe Ala Ala Arg
590                 595                 600 tca gta aga cgc agg gta gac aaa taa cgggtatctt taagtagata          2524
Ser Val Arg Arg Arg Val Asp Lys
605                 610 aggtagtaag tcgcttgggt tgcacgctta ataaagcaat caagagctat ttcataaaag  2584 ttaaccccg agttgtatta cccgtggcaa ctcgggggat tatagttttc ttttatgtgc   2644
aaatataacg agaaaatgga tacaaataga cagtgaagaa gtttattatt gcaattattg  2704
cgctggtctt attgggcgcc ggcatatatg gaaataccgg cggcgatcaa gatattgatg  2764
cgtatctagc tgaagcttta cctgaagcgc                                   2794

<210> SEQ ID NO 2
<211> LENGTH: 519
<212> TYPE: PRT
<213> ORGANISM: Dehalococcoides sp. VS

<400> SEQUENCE: 2

Met Ser Lys Phe His Lys Thr Ile Ser Arg Arg Asp Phe Met Lys Gly
1               5                   10                  15

Leu Gly Leu Ala Gly Ala Gly Ile Gly Ala Val Ala Ala Ser Ala Pro
            20                  25                  30

Val Phe His Asp Ile Asp Glu Leu Val Ser Ser Glu Ala Asn Ser Thr
        35                  40                  45

Lys Asp Gln Pro Trp Tyr Val Lys His Arg Glu His Phe Asp Pro Thr
    50                  55                  60

Ile Thr Val Asp Trp Asp Ile Phe Asp Arg Tyr Asp Gly Tyr Gln His
```

-continued

```
            65                  70                  75                  80
Lys Gly Val Tyr Glu Gly Pro Pro Asp Ala Pro Phe Thr Ser Trp Gly
                        85                  90                  95

Asn Arg Leu Gln Val Arg Met Ser Gly Glu Glu Gln Lys Lys Arg Ile
                100                 105                 110

Leu Ala Ala Lys Lys Glu Arg Phe Pro Gly Trp Asp Gly Gly Leu His
            115                 120                 125

Gly Arg Gly Asp Gln Arg Ala Asp Ala Leu Phe Tyr Ala Val Thr Gln
        130                 135                 140

Pro Phe Pro Gly Ser Gly Glu Glu Gly His Gly Leu Phe Gln Pro Tyr
145                 150                 155                 160

Pro Asp Gln Pro Gly Lys Phe Tyr Ala Arg Trp Gly Leu Tyr Gly Pro
                165                 170                 175

Pro His Asp Ser Ala Pro Pro Asp Gly Ser Val Pro Lys Trp Glu Gly
            180                 185                 190

Thr Pro Glu Asp Asn Phe Leu Met Leu Arg Ala Ala Lys Tyr Phe
        195                 200                 205

Gly Ala Gly Gly Val Gly Ala Leu Asn Leu Ala Asp Pro Lys Cys Lys
    210                 215                 220

Lys Leu Ile Tyr Lys Lys Ala Gln Pro Met Thr Leu Gly Lys Gly Thr
225                 230                 235                 240

Tyr Ser Glu Ile Gly Gly Pro Gly Met Ile Asp Ala Lys Ile Tyr Pro
                245                 250                 255

Lys Val Pro Asp His Ala Val Pro Ile Asn Phe Lys Glu Ala Asp Tyr
            260                 265                 270

Ser Tyr Tyr Asn Asp Ala Glu Trp Val Ile Pro Thr Lys Cys Glu Ser
        275                 280                 285

Ile Phe Thr Phe Thr Leu Pro Gln Pro Gln Glu Leu Asn Lys Arg Thr
    290                 295                 300

Gly Gly Ile Ala Gly Ala Gly Ser Tyr Thr Val Tyr Lys Asp Phe Ala
305                 310                 315                 320

Arg Val Gly Thr Leu Val Gln Met Phe Ile Lys Tyr Leu Gly Tyr His
                325                 330                 335

Ala Leu Tyr Trp Pro Ile Gly Trp Gly Pro Gly Gly Cys Phe Thr Thr
            340                 345                 350

Phe Asp Gly Gln Gly Glu Gln Gly Arg Thr Gly Ala Ala Ile His Trp
        355                 360                 365

Lys Phe Gly Ser Ser Gln Arg Gly Ser Glu Arg Val Ile Thr Asp Leu
    370                 375                 380

Pro Ile Ala Pro Thr Pro Ile Asp Ala Gly Met Phe Glu Phe Cys
385                 390                 395                 400

Lys Thr Cys Tyr Ile Cys Arg Asp Val Cys Val Ser Gly Gly Val His
                405                 410                 415

Gln Glu Asp Glu Pro Thr Trp Asp Ser Gly Asn Trp Asn Val Gln
            420                 425                 430

Gly Tyr Leu Gly Tyr Arg Thr Asp Trp Ser Gly Cys His Asn Gln Cys
        435                 440                 445

Gly Met Cys Gln Ser Ser Cys Pro Phe Thr Tyr Leu Gly Leu Glu Asn
    450                 455                 460

Ala Ser Leu Val His Lys Ile Val Lys Gly Val Ala Asn Thr Thr
465                 470                 475                 480

Val Phe Asn Ser Phe Thr Asn Met Glu Lys Ala Leu Gly Tyr Gly
                485                 490                 495
```

```
Asp Leu Thr Met Glu Asn Ser Asn Trp Trp Lys Glu Glu Gly Pro Ile
            500                 505                 510
Tyr Gly Phe Asp Pro Gly Thr
        515
```

<210> SEQ ID NO 3
<211> LENGTH: 93
<212> TYPE: PRT
<213> ORGANISM: Dehalococcoides sp. VS

<400> SEQUENCE: 3

```
Met Asp Ala Ile Tyr Phe Phe Leu Thr Ile Ala Leu Ala Val Gly Leu
1               5                   10                  15
Thr Met Leu Phe Thr Trp Phe Lys Lys Asn Asn Ile Thr Leu Lys Trp
            20                  25                  30
Asn Glu Trp Val Leu Gly Ile Leu Gly Leu Leu Ala Leu Phe Ala
        35                  40                  45
Ile Gln His Thr Tyr Ala Ser Ala Thr Tyr Glu Phe Glu Tyr Thr Ser
    50                  55                  60
Ala Trp Ile Val Gly Val Ile Val Leu Leu Ala Val Val Pro Leu
65                  70                  75                  80
Leu Phe Ala Ala Arg Ser Val Arg Arg Val Asp Lys
                85                  90
```

<210> SEQ ID NO 4
<211> LENGTH: 20
<212> TYPE: PRT
<213> ORGANISM: Dehalococcoides sp. VS

<400> SEQUENCE: 4

```
Glu Ala Asn Ser Thr Lys Asp Gln Pro Trp Tyr Val Lys His Arg Glu
1               5                   10                  15
His Phe Asp Pro
            20
```

<210> SEQ ID NO 5
<211> LENGTH: 11
<212> TYPE: PRT
<213> ORGANISM: Dehalococcoides sp. VS

<400> SEQUENCE: 5

```
Asp Ala Leu Phe Tyr Ala Val Thr Gln Pro Phe
1               5                   10
```

<210> SEQ ID NO 6
<211> LENGTH: 20
<212> TYPE: DNA
<213> ORGANISM: Dehalococcoides sp. VS

<400> SEQUENCE: 6
acvaargayc arccdtggta                                           20

<210> SEQ ID NO 7
<211> LENGTH: 19
<212> TYPE: DNA
<213> ORGANISM: Dehalococcoides sp. VS

<400> SEQUENCE: 7
ttytaygcmg tacvcarcc                                            19

<210> SEQ ID NO 8
<211> LENGTH: 24

```
<212> TYPE: DNA
<213> ORGANISM: Dehalococcoides sp. VS

<400> SEQUENCE: 8
ctattttacg ccgtcaccca acct                                        24

<210> SEQ ID NO 9
<211> LENGTH: 24
<212> TYPE: DNA
<213> ORGANISM: Dehalococcoides sp. VS

<400> SEQUENCE: 9
tgtaatcgta gggtcaaaat gctc                                        24

<210> SEQ ID NO 10
<211> LENGTH: 19
<212> TYPE: DNA
<213> ORGANISM: Dehalococcoides sp. VS

<400> SEQUENCE: 10
acgcgagatg gggtttgta                                              19

<210> SEQ ID NO 11
<211> LENGTH: 23
<212> TYPE: DNA
<213> ORGANISM: Dehalococcoides sp. VS

<400> SEQUENCE: 11
aattcgcttc ttttgctctt cac                                         23

<210> SEQ ID NO 12
<211> LENGTH: 24
<212> TYPE: DNA
<213> ORGANISM: Dehalococcoides sp. VS

<400> SEQUENCE: 12
gcaaaacggc agacaggtat tatc                                        24

<210> SEQ ID NO 13
<211> LENGTH: 20
<212> TYPE: DNA
<213> ORGANISM: Dehalococcoides sp. VS

<400> SEQUENCE: 13
gccacgccca actgaatagg                                             20

<210> SEQ ID NO 14
<211> LENGTH: 20
<212> TYPE: DNA
<213> ORGANISM: Dehalococcoides sp. VS

<400> SEQUENCE: 14
acvaargayc arccdtggta                                             20

<210> SEQ ID NO 15
<211> LENGTH: 18
<212> TYPE: DNA
<213> ORGANISM: Dehalococcoides sp. VS

<400> SEQUENCE: 15
tyggtccytc ytcyttcc                                               18

<210> SEQ ID NO 16
<211> LENGTH: 21
```

-continued

```
<212> TYPE: DNA
<213> ORGANISM: Dehalococcoides sp. VS

<400> SEQUENCE: 16
ctatgaaggc cctccagatg c                                          21

<210> SEQ ID NO 17
<211> LENGTH: 23
<212> TYPE: DNA
<213> ORGANISM: Dehalococcoides sp. VS

<400> SEQUENCE: 17
gtaacagccc caatatgcaa gta                                        23

<210> SEQ ID NO 18
<211> LENGTH: 21
<212> TYPE: DNA
<213> ORGANISM: Dehalococcoides sp. VS

<400> SEQUENCE: 18
tgctggtggc gttggtgctc t                                          21

<210> SEQ ID NO 19
<211> LENGTH: 21
<212> TYPE: DNA
<213> ORGANISM: Dehalococcoides sp. VS

<400> SEQUENCE: 19
tgcccgtcaa aagtggtaaa g                                          21

<210> SEQ ID NO 20
<211> LENGTH: 22
<212> TYPE: DNA
<213> ORGANISM: Dehalococcoides sp. VS

<400> SEQUENCE: 20
cttggcatat tggggctgtt ac                                         22

<210> SEQ ID NO 21
<211> LENGTH: 24
<212> TYPE: DNA
<213> ORGANISM: Dehalococcoides sp. VS

<400> SEQUENCE: 21
atttgtctac cctgcgtctt actg                                       24

<210> SEQ ID NO 22
<211> LENGTH: 20
<212> TYPE: DNA
<213> ORGANISM: Dehalococcoides sp. VS

<400> SEQUENCE: 22
gtggccctct tacggttgtt                                            20

<210> SEQ ID NO 23
<211> LENGTH: 23
<212> TYPE: DNA
<213> ORGANISM: Dehalococcoides sp. VS

<400> SEQUENCE: 23
ctaagtggcg agaaagaata atg                                        23

<210> SEQ ID NO 24
<211> LENGTH: 23
```

```
<212> TYPE: DNA
<213> ORGANISM: Dehalococcoides sp. VS

<400> SEQUENCE: 24
aaaatagtaa aaggtgttgt tgc                                          23

<210> SEQ ID NO 25
<211> LENGTH: 22
<212> TYPE: DNA
<213> ORGANISM: Dehalococcoides sp. VS

<400> SEQUENCE: 25
tatttgtcta ccctgcgtct ta                                           22

<210> SEQ ID NO 26
<211> LENGTH: 21
<212> TYPE: DNA
<213> ORGANISM: Dehalococcoides sp. VS

<400> SEQUENCE: 26
tgcggcaaga tcagtaagac g                                            21

<210> SEQ ID NO 27
<211> LENGTH: 24
<212> TYPE: DNA
<213> ORGANISM: Dehalococcoides sp. VS

<400> SEQUENCE: 27
gtaagagggc caccataacc atag                                         24

<210> SEQ ID NO 28
<211> LENGTH: 20
<212> TYPE: DNA
<213> ORGANISM: Dehalococcoides sp. VS

<400> SEQUENCE: 28
tatctttgcg tattttgtgc                                              20

<210> SEQ ID NO 29
<211> LENGTH: 18
<212> TYPE: DNA
<213> ORGANISM: Dehalococcoides sp. VS

<400> SEQUENCE: 29
gcccgctgat ccctctc                                                 18

<210> SEQ ID NO 30
<211> LENGTH: 23
<212> TYPE: DNA
<213> ORGANISM: Dehalococcoides sp. VS

<400> SEQUENCE: 30
ttgtactgag gaaacgctta tgg                                          23

<210> SEQ ID NO 31
<211> LENGTH: 19
<212> TYPE: DNA
<213> ORGANISM: Dehalococcoides sp. VS

<400> SEQUENCE: 31
gcccgctgat ccctctcc                                                19

<210> SEQ ID NO 32
<211> LENGTH: 24
```

```
<212> TYPE: DNA
<213> ORGANISM: Dehalococcoides sp. VS

<400> SEQUENCE: 32
cttatggata tttggcgttc agga                                        24

<210> SEQ ID NO 33
<211> LENGTH: 24
<212> TYPE: DNA
<213> ORGANISM: Dehalococcoides sp. VS

<400> SEQUENCE: 33
aattcgcttc ttttgctctt cacc                                        24

<210> SEQ ID NO 34
<211> LENGTH: 20
<212> TYPE: PRT
<213> ORGANISM: Dehalococcoides sp. VS

<400> SEQUENCE: 34

Glu Ala Asn Ser Thr Lys Asp Gln Pro Trp Tyr Val Lys His Arg Glu
1               5                   10                  15

His Phe Asp Pro
            20

<210> SEQ ID NO 35
<211> LENGTH: 13
<212> TYPE: PRT
<213> ORGANISM: Dehalococcoides sp. VS

<400> SEQUENCE: 35

Val Tyr Glu Gly Pro Pro Asp Ala Pro Phe Thr Ser Thr
1               5                   10

<210> SEQ ID NO 36
<211> LENGTH: 9
<212> TYPE: PRT
<213> ORGANISM: Dehalococcoides sp. VS

<400> SEQUENCE: 36

Val Gly Thr Leu Val Gln Met Phe Leu
1               5

<210> SEQ ID NO 37
<211> LENGTH: 13
<212> TYPE: PRT
<213> ORGANISM: Dehalococcoides sp. VS

<400> SEQUENCE: 37

Asp Ala Leu Phe Tyr Ala Val Thr Gln Pro Phe Pro Gly
1               5                   10

<210> SEQ ID NO 38
<211> LENGTH: 9
<212> TYPE: PRT
<213> ORGANISM: Dehalococcoides sp. VS
<220> FEATURE:
<221> NAME/KEY: VARIANT
<222> LOCATION: (1)...(9)
<223> OTHER INFORMATION: Xaa = Any Amino Acid

<400> SEQUENCE: 38

Glu Ser Ile Xaa Thr Phe Thr Leu Pro
1               5
```

-continued

```
<210> SEQ ID NO 39
<211> LENGTH: 20
<212> TYPE: PRT
<213> ORGANISM: Dehalococcoides sp. VS

<400> SEQUENCE: 39

Ala Val Arg Glu Gln Val Tyr Gly Phe Phe Ile Pro Ser Val Thr Leu
1               5                   10                  15

Ile Gly Ile Gly
            20

<210> SEQ ID NO 40
<211> LENGTH: 21
<212> TYPE: PRT
<213> ORGANISM: Dehalococcoides sp. VS

<400> SEQUENCE: 40

Ala Asn Gln Asp Trp Ser Lys Ile Ser Leu Pro Gly Ser Gly Ala Thr
1               5                   10                  15

Gly Gly Ala Tyr Val
            20

<210> SEQ ID NO 41
<211> LENGTH: 177
<212> TYPE: PRT
<213> ORGANISM: D. ethenogenes

<400> SEQUENCE: 41

Met Gly Asn Glu Arg Asp Met Asp Leu Asn Asn Ile Lys Gln Gln Glu
1               5                   10                  15

Asp Arg Ile Asn Thr Tyr Gly Glu Glu Tyr Val Asn Leu Ser Leu Met
                20                  25                  30

Ser Ile Ile Thr Leu Ile Gly Thr Ile Ala Met Arg Asn Tyr Lys Tyr
            35                  40                  45

Thr Met Gly Glu Tyr Ser Glu Asn Leu Thr Pro Asn Glu Ser Ser Leu
        50                  55                  60

Leu Met Glu Val Tyr Phe Arg Glu Glu Ile Gly Ile Ile Asp Ala Cys
65                  70                  75                  80

Arg Ala Thr Gly Leu Ser Thr Glu Asn Val Leu His Leu Phe Ser Asn
                85                  90                  95

Ile Tyr Asn Lys Gly Tyr Leu Lys Lys Val Lys Lys Gly Lys Lys Thr
            100                 105                 110

Tyr Tyr Ser Ile Ala Asp Asn Pro Pro Gly Asp Trp Gln Asp Val Leu
        115                 120                 125

Glu Gly Tyr Gln Lys Ala Thr Asp Ala Cys Asn Tyr Phe Cys Lys Asp
    130                 135                 140

Leu Ser Asp Glu Lys Lys Gln Glu Ile Trp Asp Met Leu Leu Asp Ile
145                 150                 155                 160

Arg His Asn Val Asn Asp Tyr His Val Arg Met Ser Gly Ile Ser Phe
                165                 170                 175

Leu

<210> SEQ ID NO 42
<211> LENGTH: 141
<212> TYPE: PRT
<213> ORGANISM: S. multivorans

<400> SEQUENCE: 42

His Ser Glu Cys Leu Thr Gly Asp Ala Leu Gly Ser Leu Lys Cys Asp
1               5                   10                  15
```

Cys Gly Glu Gln Leu Glu Phe Ala Leu Gln Asn Ile Ser Leu Leu Gly
                20                  25                  30

Gly Met Ile Ile Tyr Leu Arg Gln Glu Gly Arg Asn Ile Gly Leu Phe
                35                  40                  45

Asn Lys Val Asn Ala Tyr Ala Leu Gln Asp Gln Gly Phe Asp Thr Ile
                50                  55                  60

Glu Ala Asn His Gln Leu Gly Phe Lys Ser Asp Glu Arg Ser Tyr Glu
65                  70                  75                  80

Val Val Glu Thr Ile Leu Glu His Phe Lys Ile Asp Lys Ile Arg Leu
                    85                  90                  95

Leu Thr Asn Asn Pro Lys Lys Met Ser Cys Leu Lys Asn Ile Met Ile
                100                 105                 110

Ile Glu Arg Trp Pro Ile Ile Ile Pro Ser Asn Asn His Asn Val Asp
                115                 120                 125

Tyr Leu Lys Thr Lys Lys Glu Met Met Gly His Leu Leu
                130                 135                 140

<210> SEQ ID NO 43
<211> LENGTH: 551
<212> TYPE: PRT
<213> ORGANISM: Desulfitobacterium sp. Y51

<400> SEQUENCE: 43

Met Gly Glu Ile Asn Arg Arg Asn Phe Leu Lys Val Ser Ile Leu Gly
1               5                   10                  15

Ala Ala Ala Ala Ala Val Ala Ser Ala Ser Ala Val Lys Gly Met Val
                20                  25                  30

Ser Pro Leu Val Ala Asp Ala Ala Asp Ile Val Ala Pro Ile Thr Glu
                35                  40                  45

Thr Ser Glu Phe Pro Tyr Lys Val Asp Ala Lys Tyr Gln Arg Tyr Asn
                50                  55                  60

Ser Leu Lys Asn Phe Phe Glu Lys Thr Phe Asp Pro Glu Ala Asn Lys
65                  70                  75                  80

Thr Pro Ile Lys Phe His Tyr Asp Asp Val Ser Lys Ile Thr Gly Lys
                    85                  90                  95

Lys Asp Thr Gly Lys Asp Leu Pro Thr Leu Asn Ala Glu Arg Leu Gly
                100                 105                 110

Ile Lys Gly Arg Pro Ala Thr His Thr Glu Thr Ser Ile Leu Phe His
                115                 120                 125

Thr Gln His Leu Gly Ala Met Leu Thr Gln Arg His Asn Glu Thr Gly
                130                 135                 140

Trp Thr Gly Leu Asp Glu Ala Leu Asn Ala Gly Ala Trp Ala Val Glu
145                 150                 155                 160

Phe Asp Tyr Ser Gly Phe Asn Ala Thr Gly Gly Pro Gly Ser Val
                    165                 170                 175

Ile Pro Leu Tyr Pro Ile Asn Pro Met Thr Asn Glu Ile Ala Asn Glu
                180                 185                 190

Pro Val Met Val Pro Gly Leu Tyr Asn Trp Asp Asn Ile Asp Val Glu
                195                 200                 205

Ser Val Arg Gln Gln Gly Gln Gln Trp Lys Phe Glu Ser Lys Glu Glu
                210                 215                 220

Ala Ser Lys Ile Val Lys Lys Ala Thr Arg Leu Leu Gly Ala Asp Leu
225                 230                 235                 240

Val Gly Ile Ala Pro Tyr Asp Glu Arg Trp Thr Tyr Ser Thr Trp Gly
                    245                 250                 255

```
Arg Lys Ile Tyr Lys Pro Cys Lys Met Pro Asn Gly Arg Thr Lys Tyr
            260                 265                 270

Leu Pro Trp Asp Leu Pro Lys Met Leu Ser Gly Gly Val Glu Val
            275                 280                 285

Phe Gly His Ala Lys Phe Glu Pro Asp Trp Glu Lys Tyr Ala Gly Phe
            290                 295                 300

Lys Pro Lys Ser Val Ile Val Phe Val Leu Glu Glu Asp Tyr Glu Ala
305                 310                 315                 320

Ile Arg Thr Ser Pro Ser Val Ile Ser Ser Ala Thr Val Gly Lys Ser
            325                 330                 335

Tyr Ser Asn Met Ala Glu Val Ala Tyr Lys Ile Ala Val Phe Leu Arg
            340                 345                 350

Lys Leu Gly Tyr Tyr Ala Ala Pro Cys Gly Asn Asp Thr Gly Ile Ser
            355                 360                 365

Val Pro Met Ala Val Gln Ala Gly Leu Gly Glu Ala Gly Arg Asn Gly
            370                 375                 380

Leu Leu Ile Thr Gln Lys Phe Gly Pro Arg His Arg Ile Ala Lys Val
385                 390                 395                 400

Tyr Thr Asp Leu Glu Leu Ala Pro Asp Lys Pro Arg Lys Phe Gly Val
            405                 410                 415

Arg Glu Phe Cys Arg Leu Cys Lys Lys Cys Ala Asp Ala Cys Pro Ala
            420                 425                 430

Gln Ala Ile Ser His Glu Lys Asp Pro Lys Val Leu Gln Pro Glu Asp
            435                 440                 445

Cys Glu Val Ala Glu Asn Pro Tyr Thr Glu Lys Trp His Leu Asp Ser
450                 455                 460

Asn Arg Cys Gly Ser Phe Trp Ala Tyr Asn Gly Ser Pro Cys Ser Asn
465                 470                 475                 480

Cys Val Ala Val Cys Ser Trp Asn Lys Val Glu Thr Trp Asn His Asp
            485                 490                 495

Val Ala Arg Val Ala Thr Gln Ile Pro Leu Leu Gln Asp Ala Ala Arg
            500                 505                 510

Lys Phe Asp Glu Trp Phe Gly Tyr Asn Gly Pro Val Asn Pro Asp Glu
            515                 520                 525

Arg Leu Glu Ser Gly Tyr Val Gln Asn Met Val Lys Asp Phe Trp Asn
            530                 535                 540

Asn Pro Glu Ser Ile Lys Gln
545                 550

<210> SEQ ID NO 44
<211> LENGTH: 447
<212> TYPE: PRT
<213> ORGANISM: Desulfitobacterium chlororespirans

<400> SEQUENCE: 44

Met Glu Asn Asn Glu Gln Arg Gln Gln Thr Gly Met Asn Arg Arg Ser
1               5                   10                  15

Phe Leu Lys Val Gly Ala Ala Ala Thr Thr Met Gly Val Ile Gly Ala
            20                  25                  30

Ile Lys Ala Pro Ala Lys Val Ala Asn Ala Ala Glu Thr Met Asn Tyr
            35                  40                  45

Val Pro Gly Pro Thr Asn Ala Arg Ser Lys Leu Arg Pro Val His Asp
            50                  55                  60

Phe Ala Gly Ala Lys Val Arg Phe Val Glu Asn Asn Asp Glu Trp Leu
65                  70                  75                  80
```

```
Gly Thr Thr Lys Ile Ile Ser Lys Val Lys Thr Ser Glu Ala Asp
                85                  90                  95
Ala Gly Phe Met Gln Ala Val Arg Gly Leu Tyr Gly Pro Asp Pro Gln
            100                 105                 110
Arg Gly Phe Phe Gln Phe Ile Ala Lys His Pro Phe Gly Gly Thr Ile
            115                 120                 125
Ser Trp Ala Arg Asn Leu Ile Ala Ala Glu Asp Val Val Asp Gly Asp
            130                 135                 140
Ala Glu Pro Thr Lys Thr Pro Ile Pro Asp Pro Glu Gln Met Ser Gln
145                 150                 155                 160
His Ile Arg Asp Cys Cys Tyr Phe Leu Arg Ala Asp Glu Val Gly Ile
                165                 170                 175
Gly Lys Met Pro Glu Tyr Gly Tyr Tyr Thr His His Val Ser Asp Thr
            180                 185                 190
Val Gly Leu Met Ser Lys Pro Val Glu Glu Cys Val Thr Pro Val Thr
            195                 200                 205
Lys Ile Tyr Pro Asn Val Ile Val Val Met Ile Asp Gln Gly Ile Glu
        210                 215                 220
Thr Met Trp Ala Ser Thr Gly Tyr Asp Gly Ile Ser Gly Ala Met Ser
225                 230                 235                 240
Met Gln Ser Tyr Phe Thr Ser Gly Cys Ile Ala Val Ile Met Ala Lys
                245                 250                 255
Tyr Ile Gly Thr Leu Gly Tyr Asn Ala Arg Ala His His Ala Lys Asn
            260                 265                 270
Tyr Glu Ala Ile Met Pro Val Cys Ile Met Ala Ala Gly Leu Gly Glu
            275                 280                 285
Leu Ser Arg Thr Gly Asp Cys Ala Ile His Pro Arg Leu Gly Tyr Arg
        290                 295                 300
His Lys Val Ala Ala Val Thr Thr Asp Leu Pro Leu Ala Pro Asp Lys
305                 310                 315                 320
Pro Ile Asp Phe Gly Leu Leu Asp Phe Cys Arg Val Cys Lys Lys Cys
                325                 330                 335
Ala Asp Asn Cys Pro Asn Asp Ala Ile Thr Phe Asp Glu Asp Pro Val
            340                 345                 350
Glu Tyr Asn Gly Tyr Leu Arg Trp Asn Ser Asp Phe Lys Lys Cys Thr
            355                 360                 365
Glu Phe Arg Thr Thr Asn Glu Glu Gly Ser Ser Cys Gly Thr Cys Leu
            370                 375                 380
Lys Val Cys Pro Trp Asn Ser Lys Glu Asp Ser Trp Phe His Lys Ala
385                 390                 395                 400
Gly Val Trp Val Gly Ser Lys Gly Glu Ala Ala Ser Thr Phe Leu Lys
                405                 410                 415
Ser Ile Asp Asp Ile Phe Gly Tyr Gly Thr Glu Thr Ile Glu Lys Tyr
            420                 425                 430
Lys Trp Trp Leu Glu Trp Pro Glu Lys Tyr Pro Leu Lys Pro Met
            435                 440                 445
```

MICROBIAL REDUCTIVE DEHALOGENATION OF VINYL CHLORIDE

This application is a 371 National Phase Application of International Application No. PCT/US05/27565 filed Aug. 2, 2005, which claims the benefit of priority to U.S. Provisional Patent Application No. 60/598,459 filed Aug. 2, 2004 hereby expressly incorporated by reference in its entirety.

This invention was made with Government support under Government Grant DACA72-00-C-0010, awarded by the Department of the Army; DE-FG07-99ER62883, awarded by the Department of Energy; and 825689016 awarded by the Environmental Protection Agency. The Government has certain rights in this invention.

Contamination of groundwater with the chlorinated solvents tetrachloroethene (PCE) and trichloroethene (TCE) threatens numerous drinking water supplies. Conventional approaches for groundwater remediation have placed a multi billion dollar burden on society and consequently stimulated research in alternative clean-up strategies. One such strategy, the removal of these contaminants by naturally occurring, chloroethene-degrading microorganisms (bioremediation) appears to be a viable and cost-effective alternative.

The microbial degradation of PCE and TCE has been observed most frequently under anaerobic conditions where the chlorinated ethenes can be reductively dehalogenated via the lesser chlorinated ethenes cis-1,2-dichloroethene (cDCE) and vinyl chloride (VC) to harmless ethene. However, at many chloroethene-contaminated sites, reductive dehalogenation ceases, or is significantly slowed down, at the level of VC, resulting in its accumulation. Because VC is a known human carcinogen and the most toxic compound of all chloroethenes, reduction of VC to ethene is the key step in the complete anaerobic degradation of these compounds.

Reductive dehalogenation of VC has been linked to the genus *Dehalococcoides* (Cupples et al. (2003) Appl. Environ. Microbiol. 69:953-959; He et al. (2003) Appl. Environ. Microbiol. 69:996-1003; He et al. (2003) Nature 424:62-65; Hendrickson et al. (2002) Appl. Environ. Microbiol. 68:485-495; Maymó-Gatell et al. (1997) Science 276:1568-1571).

*Dehalococcoides ethenogenes* strain 195, the first microorganism isolated in pure culture that dehalogenates VC to ethene, catalyzes this reduction only in a slow, co-metabolic reaction (Magnuson et al. (2000) Appl. Environ. Microbiol. 66:5141-5147; Magnusen et al., (1998) Appl. Environ. Microbiol. 64:1270-1275; Maymó-Gatell et al. (2001) Environ Sci. Technol. 35:516-521). Recently, enrichment cultures containing *Dehalococcoides*-like organisms which couple VC reduction with energy conservation have been reported. The isolation of an axenic culture of one of those organisms, strain BAV1, was described subsequently.

While reductive dehalogenation of higher chlorinated ethenes and of some chlorinated aromatic compounds has been studied on a biochemical, chemical, and genetic level, little is known about molecular features of reductive dehalogenation of VC. In *D. ethenogenes* 195, VC-reduction is mediated by the TCE-reductive dehalogenase (TceA). The VC-reduction rate of TceA is, however, less than 1% of its activity of TCE- and cDCE-reduction.

Preliminary results have shown that VC-degrading enrichment mixed cultures have a membrane-bound activity that reduces VC and cDCE, but not TCE or PCE, with high rates, thus differing from the activity of *D. ethenogenes* 195 (see Rosner et al. (1997) Appl. Environ. Microbiol. 63:4139-4144). Isolation of the organism and characterization of the enzymes responsible for the activity is of great interest for monitoring and promoting microbial degradation of chloroethene contaminants.

SUMMARY OF THE INVENTION

Compositions and methods are provided that relate to the bioremediation of chlorinated ethenes, particularly the bioremediation of vinyl chloride by *Dehalococcoides*-like organisms. An isolated strain of bacteria, *Dehalococcoides* sp. strain VS, that metabolizes vinyl chloride is provided; the genetic sequence of the enzyme responsible for vinyl chloride dehalogenation; methods of assessing the capability of endogenous organisms at an environmental site to metabolize vinyl chloride; and a method of using the strains of the invention for bioremediation.

Using isolated *Dehalococcoides* sp. strain VS, the genetic sequence of VC-reductase was determined. This sequence is found by molecular probing to be present both in VC-dehalogenating mixed cultures used in bioremediation approaches and in groundwater samples from a contaminated field site undergoing bioremediation. By determining the presence of VC reductase specific sequences at an environmental site, the capacity of the endogenous microorganisms to dehalogenate VC can be assessed. Where this capability is absent, the appropriate organisms may be introduced.

VC reductase nucleic acid compositions and their encoded polypeptides and variants thereof are provided. VC reductases are novel sequences providing for the metabolism of vinyl chloride. In addition to providing a specific indicator of the metabolic capabilities of microorganisms, VC reductases are utilized in screening and research methods for the determination of structural features and design of altered substrate specificities and interactions, introducing dehalogenation capability to organisms. The nucleic acid compositions find use in identifying homologous or related genes; for production of the encoded protein; in producing compositions that modulate the expression or function of its encoded protein; mapping functional regions of the protein; and in studying associated physiological pathways.

The invention also provides diagnostics and kits comprising one or more of probes specific for VC reductase nucleic acids; primers suitable for amplification of VC reductase sequences; and/or antibodies specific for one or more epitopes of the VC reductase polypeptide. Such kits may further comprise sequences suitable for identifying the presence of anaerobic bacteria, including *Dehalococcoides* species, e.g. 16S RNA probes.

BRIEF DESCRIPTION OF THE DRAWINGS

FIG. 3. Amino acid sequence alignment of VcrA from *Dehalococcoides* sp. strain VS with TceA from *D. ethenogenes* (accession number AF228507, SEQ ID NO:41), PceA from *S. multivorans* (accession number AF022812 SEQ ID NO:42), PceA from *Desulfitobacterium* sp. strain Y51 (accession number AB070709, SEQ ID NO:43), and CprA from *D. dehalogenans* (accession number AF204275, SEQ ID NO:44). Amino acid residues identical in all 5 sequences are highlighted in black. Functionally similar amino acid residues (2 distance units) and amino acid residues that are conserved in only some of the sequences are boxed. Horizontal bar, twin-arginine motif; plus sign, first amino acid residue, E 44, of the mature VcrA; asterisks, conserved cysteines.

FIG. 6. VC (squares) and ethene (triangles) by Victoria (A), KB-1 (B) and Pinellas (C) cultures. Following the formation of 5 μmol of ethene (day 18 for A and B, day 21 for C), culture (200 μL) was transferred to triplicate media bottles and VC was added (200 μL), with the results shown. Error bars, following these transfers, represent standard deviations for triplicate samples. Lines do not represent model simulations.

FIG. 7. DCE (circles), VC (squares) and ethene (triangles) mass change with time in *D. ethenogenes* strain 195 cultures. Cultures were supplied with either VC (A) or DCE (B). Lines do not represent model simulations.

FIG. 8. VC (squares) and ethene (diamonds) by Victoria, KB-1/VC and Pinellas cultures inoculated with 9, 3, 1, 0.3 or 0.1 mL of culture. Lines represent model simulations as discussed in the text.

FIG. 9. Reductive dehalogenation of DCE to ethene by (A) Victoria culture, (B) KB-1/VC culture, and (C) Pinellas culture. Symbols represent DCE (diamonds), VC (triangles), and ethene (circles). Lines represent model simulations as discussed in the text.

FIG. 10(A-D). Reductive dehalogenation of TCE to ethene by the Pinellas culture. Symbols represent TCE (squares), DCE (diamonds), VC (triangles), and ethene (circles). Lines represent model simulations as discussed in the text.

FIG. 11. TCE (A), DCE (B), VC (C) dechlorination and ethene formation (D) in duplicates of the VC enrichment of strain VS from the Victoria culture. Lines represent model simulations, as discussed in the text.

FIG. 12. VC dechlorination (A) and ethene formation (B) in duplicates of the VC enrichment of strain VS. Lines represent model simulations, as discussed in the text.

FIG. 13. Comparison of mass dechlorinated (μmol chloride produced) with time by the VC enrichment of strain VS supplied with either TCE (triangles and crosses) or VC (squares and diamonds).

DETAILED DESCRIPTION OF THE INVENTION

Figure 1:
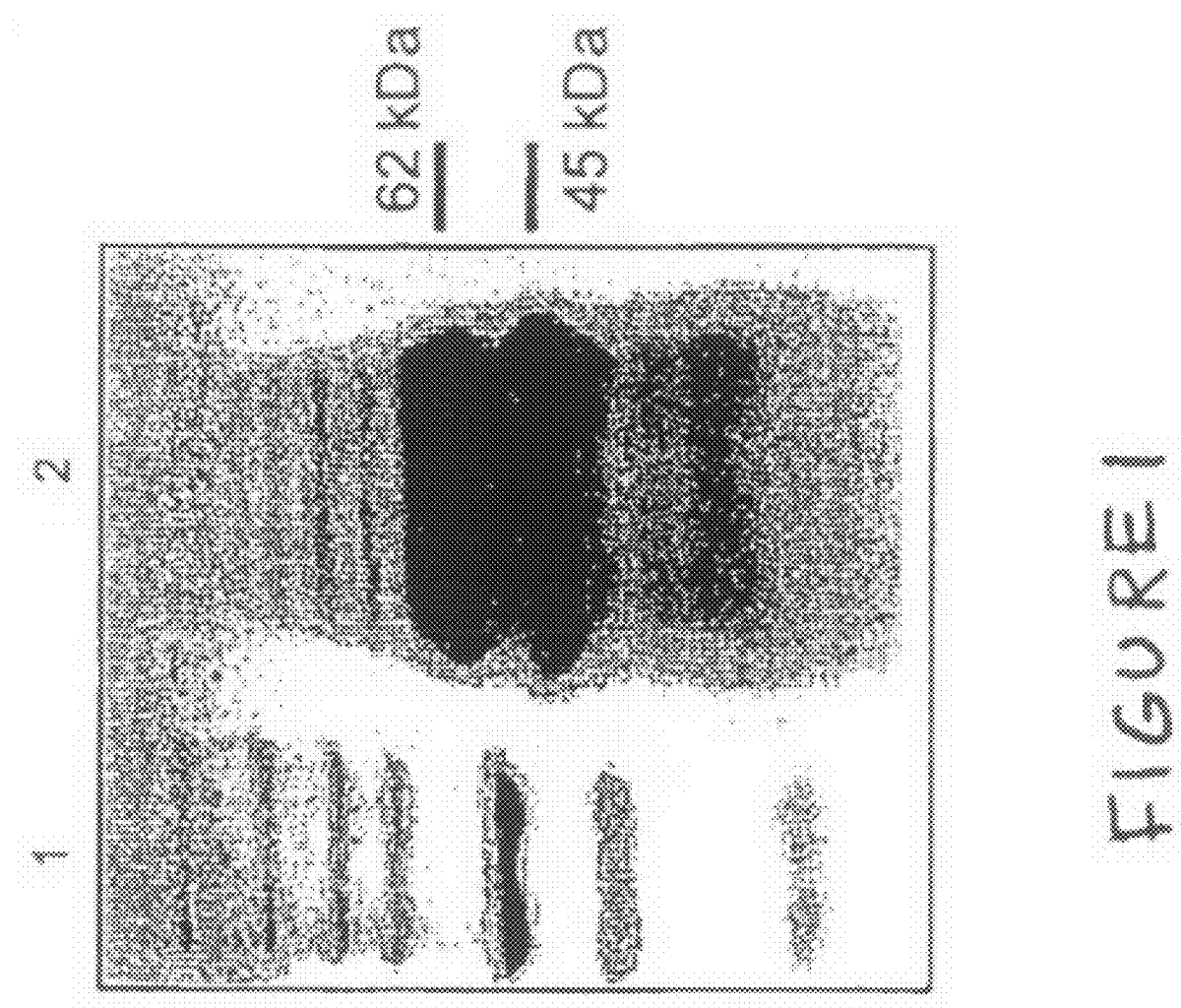
FIG. 1. SDS-polyacrylamide gel of partially purified VC-reductive dehalogenase (7 µg) of *Dehalococcoides* sp. strain VS. Lane 1, molecular weight standard (BioRad) with sizes (in kDa) of 250, 150 100, 75, 50, 37, and 25; lane 2, active fraction after gel filtration with sizes of major peptides indicated. The gel was stained with Coomassie Brilliant Blue R-250.

An isolated strain of *Dehalococcoides* that metabolizes vinyl chloride is provided. Using the isolated *Dehalococcoides* sp. strain VS, the genetic sequence of a VC-reductase was determined. By determining the presence of VC reductase specific sequences at an environmental site, the capacity of the endogenous microorganisms to dehalogenate VC can be assessed. Where this capability is absent, the appropriate organisms may be introduced.

VC reductase nucleic acid compositions and their encoded polypeptides and variants thereof are also provided. Diagnostics and kits comprising one or more of probes specific for VC reductase nucleic acids; primers suitable for amplification of VC reductase sequences; and/or antibodies specific for one or more epitopes of the VC reductase polypeptide may be used in the monitoring of environmental sites. Such kits may further comprise sequences suitable for identifying the presence of anaerobic bacteria, including *Dehalococcoides* species, e.g. 16S RNA probes.

This invention provides methods for monitoring and enhancing the biotransformation of halogenated hydrocarbons and more particularly of chlorinated aliphatic hydrocarbons. This invention has direct application to both the in situ and ex situ bioremediation of contaminated soil, sediment and ground water. Organic contaminants in soil, sediment and ground water may be biotransformed or broken down by naturally occurring microorganisms, or by introduced microorganisms.

Trichloroethylene (TCE) is widely used as a solvent and a degreasing agent. It has been spilled in the environment and causes great concern because of its toxicity and possible carcinogenic properties. Similarly, cis-dichloroethylene (cis-DCE), which is frequently the anaerobic transformation product of TCE, accumulates in the environment and poses an equally important health hazard.

Highly chlorinated aliphatic hydrocarbons may be biotransformed to lower chlorinated homologs by a process known as reductive dehalogenation. Chlorinated ethenes may be reductively dechlorinated by natural microbial communities and mixed microbial enrichment cultures under anaerobic conditions. For example, the reductive dechlorination of TCE occurs via cis-dichloroethylene (cis-DCE) and vinyl chloride (VC) to ethene by the sequential replacement of the chlorine atoms with hydrogen.

However, reductive dehalogenation of vinyl chloride (VC) to ethene is the key step in complete anaerobic degradation of chlorinated ethenes. Sequences of the VC reductive dehalogenase from the VC-respiring *Dehalococcoides* sp. strain VS are provided herein. The enzyme reduces VC and all dichloroethene (DCE) isomers with comparable high rates. VC reductase is a novel member of the family of corrinoid/iron-sulfur cluster containing reductive dehalogenases. The vcrAB genes are found to be present and expressed in other cultures containing VC-respiring *Dehalococcoides* organisms, and can be detected in samples from field sites contaminated with chlorinated ethenes. The vcrA gene provided herein is a useful molecular target for evaluating, predicting, and monitoring in situ reductive VC dehalogenation.

Microorganisms

Compositions are provided of an isolated microorganism, *Dehalococcoides* sp. strain VS, which is capable of reductive dehalogenation of vinyl chloride in a metabolic reaction. The organism can perform complete TCE conversion to ethene. The organism may be identified by comprising an endogenous copy of the genetic sequence provided in SEQ ID NO:1.

For the purposes of the present invention, an isolated bacterial strain is one that has undergone some degree of purification from its natural environment. A culture of a bacterium considered to be biologically pure will comprise at least about 50% of the bacteria as the desired strain, usually at least about 75%, more usually at least about 90%, and may be substantially all of the organisms present in the culture.

The bacterial strain of the present invention may also be combined with other species of bacteria, nutrients, and/or other components to provide a composition for bioaugmentation of halogenated ethene contaminated sites; for the study of pathways involved in reductive dehalogenation, and the like. It may be desirable, for example to combine the bacteria of the present invention with bacteria capable of removing other pollutants or undesirable compounds from such contaminated sites.

VC Reductase Nucleic Acids

The invention provides novel nucleic acids and polypeptides, referred to herein as a VC reductase, or vcrA. "Reductive dechlorination" is a term that refers to the process in which a chloro-organic compound as terminal electron acceptor and a chloride atom is removed from a chloro-organic compound. Also provided are novel nucleic acids that are co-transcribed with vcrA. The vcrA gene is co-transcribed with vcrB, which encodes for a small hydrophobic protein that may act as membrane anchor for VC reductase, and vcrC, which encodes a protein similar to transcriptional regulators of the NosR/NirI family. The genes may be referred to herein as members of the vcr operon. Where function of the vcrA gene is of interest, it may be co-expressed with the vcrB gene.

The VCR operon sequence is provided as SEQ ID NO:1. In the operon, vcrA is contained within the following residues: gene, SEQ ID NO:1, residues 484-2794; −35_signal, SEQ ID NO:1, residues 484-489; −10 signal, SEQ ID NO:1, residues 506-511; coding sequence, SEQ ID NO:1, residues 623-2182, with a signal peptide SEQ ID NO:1, residues 623-751. The amino acid sequence of vcrA is provided as SEQ ID NO:2. In the operon, vcrB coding sequence is SEQ ID NO:1, residues 2223-2504. The amino acid sequence of vcrB is provided as SEQ ID NO:3.

The vcrA gene is 1560 bp in length and encodes a polypeptide, VcrA, of 519 amino acids with a calculated molecular mass of 57,506 Da. The GC content of vcrA (44.6%) is similar to the GC content of the *D. ethenogenes* genome (48.9%) and the average GC content of the putative dehalogenase genes (48.3%) in this organism. Two DNA sequences upstream of vcrA were nearly identical to the −10 and −35 regions of an *E. coli* σ 70-promoter.

The leader sequence contains a twin-arginine motif (Tat-motif), and is similar to those found in other reductive dehalogenases. Two motifs for iron-sulfur clusters are found at positions 400-411 and 444-456. Both motifs are similar to the ferredoxin-type 4Fe4S-cluster (Cx2Cx2Cx3CP); here with the variations that the first motif contains a valine after the fourth cysteine instead of the canonical proline, and the second motif displays three amino acids between the first two cysteines instead of two as in the consensus sequence.

In addition to the leader sequence and the C-terminal two iron-sulfur cluster motifs, several highly conserved amino acid residues, including a conserved histidine, H469, is present in VcrA and all other reductive dehalogenases. Furthermore, the sequence in VcrA ranging from amino acid 198 to 215 displays strong similarity to a region in TceA and all putative dehalogenases from *D. ethenogenes*.

vcrB is a gene of 282 bp, located 41 bp downstream of vcrA and preceded by a putative ribosome binding site. The 94, predominantly hydrophobic amino acids account for a calculated molecular mass of 10,641 Da (VcrB). Sequence analysis shows the presence of three transmembrane spanning regions. The VcrB sequence shows identity to proposed membrane anchors (B-proteins) for reductive dehalogenases. Canonical binding motifs for redox-active cofactors, i.e, iron-sulfur cluster, heme, NAD/FAD, or flavin were not detected in VcrB.

The start codon of vcrC is 228 bp downstream of vcrB (SEQ ID NO:1, residues 2451-2794). The partial vcrC gene translates into a protein, VcrC, of at least 305 amino acids with a calculated molecular mass of at least 33,363 Da. Four potential membrane-spanning helices are predicted to occur in VcrC, which may function as a NosR/NirI-type transcriptional regulator.

The present invention includes nucleic acids having a sequence set forth in SEQ ID NO:1, including separately each of the coding sequences as set forth above; nucleic acids that hybridize under stringent conditions, particularly conditions of high stringency, to SEQ ID NO:1, or to a fragment thereof, including the coding sequences in the operon; genes corresponding to the provided nucleic acids; sequences encoding VC reductases; and fragments and derivatives thereof. Other nucleic acid compositions contemplated by and within the scope of the present invention will be readily apparent to one of ordinary skill in the art when provided with the disclosure here.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening probes, etc. Larger DNA fragments, i.e. greater than 100 or 250 nt are useful for production of the encoded polypeptide, or fragments thereof.

The vcr A, B or C genes are isolated and obtained in substantial purity, generally as other than an intact, naturally occurring chromosome. Usually, the DNA will be obtained substantially free of other nucleic acid sequences that do not include a vcr A, B or C sequence or fragment thereof, generally being at least about 50%, usually at least about 90% pure and are typically "recombinant", i.e. flanked by one or more nucleotides with which it is not normally associated on a naturally occurring chromosome.

The sequence of a vcr A, B or C gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, GFP fusions, etc.

Techniques for in vitro mutagenesis of cloned genes are known. Examples of protocols for site specific mutagenesis may be found in Gustin et al., Biotechniques 14:22 (1993); Barany, Gene 37:111-23 (1985); Colicelli et al., Mol Gen Genet. 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126: 35-41 (1993); Sayers et al., Biotechniques 13:592-6 (1992); Jones and Winistorfer, Biotechniques 12:528-30 (1992); Barton et al., Nucleic Acids Res 8:7349-55 (1990); Marotti and Tomich, Gene Anal Tech 6:67-70 (1989); and Zhu, Anal Biochem 177:120-4 (1989). Such mutated genes may be used to study structure-function relationships, to alter properties of the protein that affect its function or regulation, and the like.

The nucleic acids of the invention include nucleic acids having sequence similarity or sequence identity to SEQ ID NO:1, or to a fragment thereof, including the coding sequences in the operon. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to SEQ ID NO:1, or to a fragment thereof, including the coding sequences in the operon under stringent hybridization conditions. By using probes, particularly labeled probes of DNA sequences, one can isolate homologous or related genes.

In one embodiment, hybridization is performed using at least 18 contiguous nucleotides (nt) of SEQ ID NO:1, or a DNA encoding a vcrA, vcrB or vcrC polypeptide. Such a probe will preferentially hybridize with a nucleic acid comprising the complementary sequence, allowing the identification and retrieval of the nucleic acids that uniquely hybridize to the selected probe. Probes of greater than 18 nt can be used, e.g., probes of from about 18 nt, of from about 25, 50, 100, 250, or 500 nt, but 18 nt usually represents sufficient sequence for unique identification.

Nucleic acids of the invention also include naturally occurring variants of the nucleotide sequences (e.g., degenerate variants, allelic variants, introduced alterations in sequence, etc.) Variants of the nucleic acids of the invention are identified by hybridization of with nucleotide sequences disclosed herein, preferably by hybridization under stringent conditions. For example, by using appropriate wash conditions, variants of the nucleic acids of the invention can be identified where the variant exhibits at most about 25-30% base pair (bp) mismatches relative to the selected nucleic acid probe. Variants may contain 15-25% bp mismatches, and can contain as little as even 5-15%, or 2-5%, or 1-2% bp mismatches, as well as a single bp mismatch.

The invention also encompasses homologs corresponding to the nucleic acids of SEQ ID NO:1, or a DNA encoding the polypeptide of vcrA, vcrB or vcrC, where the source of homologous genes can be any microbial species. Homologs generally have substantial sequence similarity, e.g., at least 85% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul et al. *Nucl. Acids Res*. (1997) 25:3389-3402.

The DNA may be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA or DNA may be amplified. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 20 nt, usually at least about 50 nt, more usually at least about 100 nt, or greater. Algorithms for the selection of primer sequences are generally known, and are available in commercial software packages. Amplification primers hybridize to complementary strands of DNA, and will prime towards each other.

Alternatively, a nucleic acid sample may be transferred to a suitable support, e.g. nitrocellulose, nylon, etc., as a dot blot, following gel electrophoresis, in a microarray format, etc., and then probed with a fragment of the subject DNA as a probe. Other techniques, such as oligonucleotide ligation assays, in situ hybridizations, and hybridization to DNA probes arrayed on a solid chip may also find use. Detection of a nucleic acid hybridizing to the subject sequence is indicative of the presence of a microbial species capable of metabolizing vinyl chloride to ethene.

A genomic sequence of interest comprises the nucleic acid present between the initiation codon and the stop codon, as defined in the listed sequences. It can further include the 3' and 5' untranslated regions found in the mature mRNA. It can further include specific transcriptional and translational regulatory sequences, such as promoters, ribosome binding sites, etc., including about 1 kb, but possibly more, of flanking genomic DNA at either the 5' and 3' end of the transcribed region.

Probes specific to the nucleic acid of the invention can be generated using the nucleic acid sequence disclosed in SEQ ID NO:1; SEQ ID NO:3 or SEQ ID NO:5, or a DNA encoding the polypeptide of SEQ ID NO:2; SEQ ID NO:4 or SEQ ID NO:6. The probes are preferably at least about 18 nt, 25 nt or more of the corresponding contiguous sequence. The probes can be labeled, for example, with a radioactive, biotinylated, or fluorescent tag. Preferably, probes are designed based upon an identifying sequence of one of the provided sequences.

More preferably, probes are designed based on a contiguous sequence of one of the subject nucleic acids that remain unmasked following application of a masking program for masking low complexity (e.g., BLASTX) to the sequence, i.e., one would select an unmasked region, as indicated by the nucleic acids outside the poly-n stretches of the masked sequence produced by the masking program.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

The nucleic acid sequences may be employed for producing all or portions of Vcr polypeptides. For expression, an expression cassette may be employed. The expression vector will provide a transcriptional and translational initiation region, which may be inducible or constitutive, where the coding region is operably linked under the transcriptional control of the transcriptional initiation region. These control regions may be native to a vcr gene, or may be derived from exogenous sources. The peptide may be expressed in prokaryotes or eukaryotes in accordance with conventional ways, depending upon the purpose for expression, usually in prokaryotes. For large scale production of the protein, a host organism, such as E. coli, B. subtilis, etc., may be used as the expression host cells.

VC Reductase Polypeptides

The VC reductase polypeptide (VcrA) is a polypeptide of 519 amino acids with a calculated molecular mass of 57,506 Da. VcrB is a polypeptide of 94 predominantly hydrophobic amino acids, with calculated molecular mass of 10,641 Da. VcrC is a polypeptide of at least 305 amino acids with a calculated molecular mass of at least 33,363 Da. The amino acid sequences are provided herein. Peptides of interest include fragments of at least about 12 contiguous amino acids, more usually at least about 20 contiguous amino acids, and may comprise 30 or more amino acids, up to the provided peptide.

A modification or fragment of a Vcr peptide may be selected to achieve a specific purpose. For example, alterations in sequence may be made in one or both of the motifs for iron-sulfur clusters of VcrA at SEQ ID NO:2, positions 400-411 and 444-456; at a conserved histidine at position 469, and in the conserved region at positions 198-215. Fragments comprising these motifs are also of interest.

The sequence of the Vcr polypeptides may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation. Also embraced are sequences that have phosphorylated amino acid residues, e.g. phosphotyrosine, phosphoserine, or phosphothreonine. Also included in the subject invention are polypeptides that have been modified using ordinary molecular biological techniques and synthetic chemistry. Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

The expressed Vcr polypeptides may be used for the production of antibodies, where short fragments provide for antibodies specific for the particular polypeptide, and larger fragments or the entire protein allow for the production of antibodies over the surface of the polypeptide. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds, Cold Spring Harbor Laboratories, Cold Spring Harbor, N.Y. 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage "display" libraries, usually in conjunction with in vitro affinity maturation.

Monitoring Methods

DNA-based reagents derived from the sequence of the provided VC reductase, e.g. PCR primers, oligonucleotide or DNA probes, as well as antibodies against VC reductase, are used to screen samples, e.g. for the presence of vcr sequences. While organisms of the *Dehalococcoides* genus are commonly found in environmental sites, such organisms may lack the ability to metabolize vinyl chloride. An assessment of the competence of a site to dehalogenate VC to ethene is made by determining the presence and quantity of organisms comprising VC reductase coding sequences. Where a site lacks sufficient numbers of the appropriate organism, bioaugmentation may be performed to add such organisms to the site; to provide suitable additives to encourage the growth of such organisms; and the like.

The sample to be tested may or may not contain the organism of interest. The sample may take a variety of forms, including liquid such as water, or solid such as dust or soil. The sample nucleic acid must be made available to contact the probe before any hybridization of probe and target molecule can occur. Thus the nucleic acid must be free from the cell and placed under the proper conditions before hybridization can occur. Methods for the purification of the sample nucleic acid are common and well known in the art. Where the analyte is the VC reductase protein, methods known in the art for such sample preparation are used.

A number of methods are available for analyzing nucleic acids for the presence of a specific sequence. Genomic DNA may be used directly; alternatively, the region of interest may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. Molecular Cloning: A Laboratory Manual, CSH Press 1989, pp. 14.2-14.33. Cells that express VC reductase may be used as a source of mRNA, which may be assayed directly or reverse transcribed into cDNA for analysis.

Typical methods of primer directed amplification include polymerase chain reaction (PCR), ligase chain reaction (LCR) or Strand displacement Amplification (SDA). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 and U.S. Pat. No. 4,683,195. If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, NAD, dithiothreitol and salmon sperm DNA. Additional methods of RNA replication such as replicative RNA system (Qβ-replicase) and DNA dependent RNA-polymerase promoter systems (T7 RNA polymerase) are contemplated to be within the scope of the present invention.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein(6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g., amplified or cloned fragment, genomic DNA, mRNA, etc. is analyzed by one of a number of methods known in the art. Hybridization with a vcr probe may also be used to determine its presence, by Southern blots, microarrays, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The nucleic acid may be sequenced by dideoxy or other methods, and the sequence of bases compared to a wild-type VC reductase sequence.

A variety of PCR detection methods are known in the art including standard non-denaturing gel electrophoresis (e.g., acrylamide or agarose), denaturing gradient gel electrophoresis, and temperature gradient gel electrophoresis.

Antibodies specific for VC reductase may be used in immunoassays. The antibodies of interest are added to the sample, e.g. a lysate of cells in an environmental sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Methods are well-known in the art for the detection of an antigen with a cognate antibody, e.g. ELISA, RIA; etc. An antibody is bound to a support, which will usually result in binding of a detectable conjugate to the support in the presence of the antigen that is being detected. The antibody may be bound to the surface in any convenient manner, either covalently or non-covalently, so long as it is maintained bound to the support during the course of the assay. Methods for binding antibodies to supports are well-known in the literature and need not be described here. Any convenient support may be used, such as microtiter wells, slides, tubes, etc., where each of the individual determinations can be maintained independent of the other determinations and the label can be discretely determined. A device which fulfills the requirements of the subject determinations is a microtiter plate.

While antibodies, particularly monoclonal antibodies, are the most convenient, any other receptor which binds specifically to VC reductase may also be used. The label may be any convenient label that provides the desired degree of sensitivity. Commonly employed labels include enzymes, fluorescers, radioisotopes, and the like. Of particular interest are enzymes, where the enzyme has a substrate which provides for a colored product, particularly a colored product which can be readily detected in a spectrophotometer. The enzyme substrate solution may be varied widely, generally being the range of about 20-500 µl. Various buffers may be employed, such as phosphate, Tris, MOPS, HEPES, and the like. The concentration of the buffer will generally be sufficient to maintain the desired pH, generally being from about 10 mM to about 0.5M.

In carrying out the determination, normally both a positive and negative control will be employed. The positive control provides a base value for the presence of VC reductase. The negative control may be buffer or any other medium, control organisms, and the like.

The detection reagents can be provided as part of a kit. Thus, the invention further provides kits for detecting the presence of a nucleic acid encoding a VC reductase, and/or a polypeptide encoded thereby, in a sample. Procedures using these kits may be performed by environmental testing laboratories, as part of government monitoring of sites, and the like. The kits of the invention for detecting a polypeptide may comprise a moiety that specifically binds the polypeptide, which may be a specific antibody. The kits of the invention for detecting a nucleic acid may comprise a moiety that specifically hybridizes to such a nucleic acid, which may include primers, such as PCR primers. The kit may optionally provide additional components that are useful in the procedure, including, but not limited to, buffers, developing reagents, labels, reacting surfaces, means for detection, control samples, standards, instructions, and interpretive information.

Genetically Altered Cell or Animal Models for VC Reductase Function

The subject nucleic acids can be used to generate modified organisms, where the VC reductase capability is introduced. Because of the requirements of the metabolic pathway, such organisms will generally be anaerobes, e.g. other members of the *Dehalococcoides* genus. The modified cells are useful in the study of VC reductase function and regulation.

Bioremediation

In situ bioremediation of contaminated soil, sediments or water is generally performed by first identifying the contaminated region to be treated by sinking observation wells in a grid pattern covering the region and taking water samples from the wells or collecting soil samples in a grid pattern covering the region. The sample containing one or more environmental contaminants can include soil, sediment, sludge, water, or combinations thereof, and the bioremediation method can be carried out in situ.

Analysis is conducted on these samples to determine the concentration of halogenated or chlorinated compounds and type of compounds at the various locations in the contaminated region. Next, as described above, the site is monitored for the presence of, and if necessary to provide, vinyl chloride metabolizing organisms. This may be accomplished by sprinkling or spraying a liquid solution comprising the organisms on the surface of the contaminated region and allowing the liquid to permeate through the region. Alternatively, injection wells or other forms of conduits may be utilized. If the sample is in a subsurface environment, such as groundwater, the contacting step can include injecting a liquid into the subsurface environment using, for example, drive-point devices. Alternatively, recirculation wells can be used.

Suitable organisms for bioremediation comprise the ability to metabolize vinyl chloride, e.g. *Dehalococcoides* sp. strain VS; organisms comprising a VC reductase coding sequence; organisms genetically modified to comprise a VC reductase coding sequence; and the like. The organisms may be provided as an isolate; or as a consortium of organisms. If desired, nutrients, such as phosphorus- and nitrogen-containing compounds, can be provided to the sample containing the contaminants to support microbial activity. Such nutrients can be added to the sample as separate compounds or they can be engineered into the compound having at least one hydrolyzable organic group.

This invention is also suitable for anaerobic biotransformation a halogenated organic compound in water from an aqueous soil environment by anaerobic bacteria, for example in an above ground bioreactor. Contaminated soil can also be excavated and placed in a bioreactor. Above ground or ex situ bioremediation of aquifers frequently involves "pump and treat" operations which process and treat large volumes of contaminated ground water by use of one or more bioreactors. Generally, ex situ bioremediation of soil or water is performed by transferring the soil or water, or combinations thereof, to a bioreactor treatment process where a significant degree, if not all, of the biotransformation occurs. The organism is added to a bioreactor or upstream thereof. The amount of the organism which is added is preferably an amount that is effective to enhance biotransformation of the halogenated contaminant.

The bioremediation method can be monitored by measuring the initial concentration of a contaminant and monitoring its degradation into transformation products. This latter step can be accomplished by measuring the decrease in concentration of the contaminant of interest and/or the increase in concentration or partial pressure of its transformation products during the degradation of the environmental contaminant.

The transformation products typically include less hazardous, preferably innocuous, compounds and ions. For example, for the halogenated contaminants, the transformation products typically include less hazardous (and generally innocuous) organic compounds such as ethane and ethene, salts such as chloride salts and fluoride salts, as well as carbon dioxide, hydrogen, and water.

In another embodiment, the present invention provides a bioremediation method of degrading a halogenated organic compound in an environmental sample. The method includes: determining the presence of the halogenated organic compound; and contacting the environmental sample with at least one microorganism comprising a VC reductase.

The present invention provides bioremediation methods and kits for degrading environmental contaminants, such as chlorinated ethenes, in a sample of soil, sediment, sludge, water, or combinations thereof. For example, the sample containing an environmental contaminant can include subsurface water or soil, which can be treated either in situ or ex situ. A contaminated sample typically includes one or more types of microorganisms that degrade the contaminants at least partially. The methods of the invention provide a means of determining whether the degradation will proceed to completion, e.g. to ethene. If such a capability is absent, such microorganisms can be added to the sample.

Although this invention has been described primarily in terms of the biotransformation of chlorinated aliphatic hydrocarbons, it is clearly envisaged that the organisms; genetic sequences and polypeptides of this invention may also be useful for biotransforming other halogenated compounds such as brominated, fluorinated, and iodinated hydrocarbons to their respective lower homologs. Moreover, this invention may be suited for the biotransformation of halogenated aromatic hydrocarbons.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a mouse" includes a plurality of such mice and reference to "the cytokine" includes reference to one or more cytokines and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Materials and Methods

Materials. Titanium(III)NTA stock solutions contained 100 mM $Ti^{3+}$ chelated by 150 mM nitrilotriacetate, and were prepared as described elsewhere. FeS was prepared according to Ehrenreich and Widdel. All other chemicals and gases used were of reagent grade or better and from standard commercial sources. Fast-protein liquid chromatography (FPLC) columns were obtained from Pharmacia.

Bacterial culture and growth conditions. The VC-dehalogenating culture (Victoria-culture) was cultivated under strictly anoxic conditions in a MOPS-buffered (20 mM, pH 7.2) mineral salt water medium essentially as described in Rosner et al. (1997) Appl. Environ. Microbiol. 63:4139-4144, with the alteration of the buffering system. The culture was grown under an $N_2/H_2$ [90:10 (vol/vol)] atmosphere in 5 carboy bottles containing 4 l medium with FeS (~0.5 mmol/l) and 0.2 mM titanium(III)NTA as reducing agents. Addition of 10% of sterile-filtered supernatant of a mixed culture containing *Dehalococcoides* sp. strain VS grown with bicarbonate-buffer was needed to obtain sufficient growth. The electron acceptors VC or 1,1-DCE were added discontinuously over time in 200 µmol/l increments up to a total of 5-10 mmol/l; the electron donor $H_2$ was replenished when needed. The cultures were stirred in the dark at 30° C. for several weeks with frequent exchange of the headspace of the bottles in an anoxic chamber (Coy Laboratory Products, Ann Arbor, Mich.). The mixed cultures KB-1, Pinellas, and WS were grown in reduced mineral medium with VC as electron acceptor essentially as described previously.

Enzyme assays. Cells were harvested by centrifugation (20,000·g, 20 min, 4° C.) under strictly anoxic conditions using the anoxic chamber, washed and resuspended in degassed MOPS buffer (20 mM, pH 7.2) supplemented with 2 mM DTE and 0.2 mM titanium(III)NTA (buffer A). The buffer was incubated overnight in the anoxic chamber before addition of reducing agents. Cell-free extracts were obtained by anoxic disruption of cells by French Press treatment (138 MPa; two passages), followed by two centrifugation steps (30,000×g, 15 min, 4° C.).

Assays of VC-reduction were conducted as described previously in 2-ml glass vials under an $N_2/H_2$ atmosphere with Ti(III)-reduced methyl viologen as artificial electron donor (Rosner et al.) The protein concentration in the assay varied between 10 and 100 µg/ml. The test was started by addition of gaseous VC to the assay mix (total aqueous volume 0.3 ml), and change in VC and ethene concentrations were followed with time by gas chromatography. Experiments testing for reduction of liquid chlorinated ethenes (PCE, TCE, DCE-isomers) were carried out essentially as described above with the appropriate substitution of the chlorinated ethene. The chlorinated compounds were added from aqueous stock solutions.

Oxygen sensitivity of VC-reducing activity in cell-free extract was investigated in buffer amended with resazurin as redox indicator. Prior to addition of VC, the assay was exposed to air until the resazurin underwent a color-change from colorless to pink. Subsequently, the assay was rendered anoxic again by exchanging the gas phase inside the anoxic chamber followed by addition of Ti(III)NTA (5 mM final concentration). All enzyme assays were carried out at ambient temperature, and given activities are means of at least three independent measurements.

Partial purification of VC reductase. Protein purification was performed at 4° C. in the anoxic chamber. The membrane fraction was obtained by centrifugation of cell-free extract at 100,000×g for 90 min at 4° C. The pellet was resuspended in 1 ml buffer A supplemented with 2 mM 3-[(3-cholamidopropyl)dimethylammonio]-1-propanesulfonic acid (CHAPS), and incubated for 1 h on ice. After subsequent centrifugation (100,000×g, 90 min, 4° C.) the solubilized membrane fraction was diluted with an equal volume of buffer B (50 mM 1,3-Bis[tris(hydroxymethyl)methylamino]propane (Bis-Tris Propane), pH 9.6, 2 mM dithiothreitol, 0.2 mM titanium(III) NTA, 20 mM CHAPS), and loaded on a 1-ml HighTrap Q column (Amersham Pharmacia) equilibrated with buffer C (same as buffer B but with 2 mM CHAPS). VC reductive dehalogenase activity was eluted as a single peak (at 550 to 580 mM NaCl) with 10 ml buffer C followed by a 40-ml linear gradient from 0-700 mM NaCl in buffer C at a flow of 1 ml/min. Fractions containing the highest activity were pooled and mixed with an equal volume of buffer A containing 20 mM CHAPS, and applied to a Superose-6 column equilibrated with the same buffer. Enzyme activity was eluted with buffer A at a flow rate of 0.2 ml/min. The protein concentration of the samples was determined according to Bradford with bovine serum albumin as a standard.

Amino acid sequencing and tryptic digest. Peptides present in active enzyme fractions were separated by 12% SDS-polyacrylamide gel electrophoresis and adsorbed onto polyvinylidene difluoride membrane by electroblotting. The transferred peptides were excised and their N-termini sequenced at the Stanford Protein and Nucleic Acid (PAN) Facility. To obtain internal peptides, active enzyme fractions were separated using SDS gel electrophoresis, bands were excised, digested with trypsin, separated by High-Performance Liquid Chromotagraphy (HPLC), and sequenced.

PCR amplification, cloning and sequencing. Standard protocols were used for DNA cloning and transformation. Chromosomal DNA was purified according to Owen and Borman. Purification of PCR-products and Plasmids were performed using Qiaprep spin columns (Qiagen). Clones were generated in pETBlue-1 (Novagen) or in pDrive (Qiagen). Sequencing was carried out on an ABI Prism 373 sequencer using ABI Big-Dye sequencing chemistry (PE Applied Biosystems) at the Stanford Protein and Nucleic Acid (PAN) Facility. Southern blot analysis was performed using dioxiginin labeled probes following the Genius kit protocol (Boehringer Mannheim).

Based on the N-terminal amino acid sequence (SEQ ID NO:4 EANSTKDQPWYVKHREHFDP) and on one internal amino acid sequence (SEQ ID NO:5, DALFYAVTQPF) of the 62 kDa peptide (see below), degenerate oligonucleotides were designed: (SEQ ID NO:6) Nterm13F (5'-ACV AAR GAY CAR CCD TGG TA-3') and (SEQ ID NO:7) Intern4R (5'-TTY TAY GCM GTI ACV CAR CC-3'). PCR-conditions were as follows: 100 ng of genomic DNA, 200 nM of each primer, 200 µM dNTP, 1 U Taq Polymerase in PCR-buffer with 1.5 mM MgCl$_2$ (Roche). PCR-parameters were as follows: 3 min at 92° C., 30 cycles of 1 min at 94° C., 1 min at 47° C., 1 min at 72° C., followed by 5 min at 72° C. A single amplification product of 292 bp was cloned into pET-Blue and was used to generate a probe for Southern blot analysis.

Southern blot analysis with genomic DNA from the VC-degrading mixed culture identified a 3.0-kb HindIII fragment, a 3.0-kb AccI fragment, and a 1.6-kb SspI fragment that hybridized to the probe. Subsequently, inverse-PCR with genomic DNA from the VC-degrading mixed culture was carried out as described below. Genomic DNA was digested with SspI, the reaction mix was purified with Qiaprep spin columns, and the digested DNA ligated (0.5 ng/µl) with T4 DNA Ligase in the presence of ATP overnight at 12° C. The ligated DNA was purified with Qiagen-Plasmid Preparation and used in inverse-PCR amplification. Based on the previously determined 292 bp DNA sequence, primers (SEQ ID NO:8) vcrSspf (5'-CTA TTT TAC GCC GTC ACC CAA CCT-3') and (SEQ ID NO:9) vcrSspr (5'-TGT AAT CGT AGG GTC AAA ATG CTC-3') were designed. The reaction contained 25 ng/µl circularized DNA, 150 nM of each primer, 200 µM dNTP, 1 U Taq Polymerase in PCR-buffer with 1.5 mM MgCl$_2$, and Q-solution (Qiagen) in a total volume of 20 µl.

PCR-parameters were as follows: 3 min at 92° C., 35 cycles of 1 min at 94° C., 1 min at 56° C., 2 min at 72° C., followed by 7 min at 72° C. A single 1.4-kb fragment was amplified, cloned, and sequenced. Based on this sequence, the primer pair (SEQ ID NO:10) vcrAcc/Hinf (5'-ACG CGA GAT GGG GTT TGT A-3') and (SEQ ID NO:11) vcrAcc/Hinr (5'-AAT TCG CTT CTT TTG CTC TTC AC-3') was designed for a second round of inverse-PCR with genomic DNA digested with AccI or HindIII, respectively. The MgCl$_2$ concentration in the PCR-mixtures was raised to 2.0 mM. PCR-parameters were as follows: 3 min at 92° C., 35 cycles of 1 min at 94° C., 1 min at 51° C., 3 min at 72° C., followed by 7 min at 72° C. A single 2.8-kb fragment from each PCR-reaction was amplified, cloned, and sequenced. To obtain further downstream sequence, a new probe for Southern blotting was generated from the 3'-end of the HindIII fragment. This probe hybridized to a 1.5 kb NcoI fragment. Inverse-PCR with NcoI-digested genomic DNA yielded a 1.1-kb fragment. Primers and PCR-parameters were as follows: (SEQ ID NO:12) vcrNcof (5'-GCA AAA CGG CAG ACA GGTA TTA TC-3') and (SEQ ID NO:13) vcrNcor (5'-GCC ACG CCC AAC TGA ATA GG-3'); 3 min at 92° C., 35 cycles of 1 min at 94° C., 1 min at 56° C., 3 min at 72° C., followed by 7 min at 72° C. The sequences of vcrA and vcrB were verified by PCR-amplification with Pfu polymerase (Stratagene) and sequencing products from three independent PCR assays.

For PCR-amplification of vcrAB operons from other VC-degrading mixed cultures (KB-1, Pinellas-culture, WS) the following degenerate primers were designed: (SEQ ID NO:14) 5'-ACVAARGAYCARCCDTGGTA-3' and (SEQ ID NO:15) 5'-TYGGTCCYTCYTCYTTCC-3'. A single 1392 bp product was obtained from each culture, cloned, and sequenced. The flanking regions of those products were PCR-amplified using primers designed from the vcrAB genomic locus of strain VS. The possibility of a contamination of the three mixed cultures with strain VS was excluded by amplification of the vcrAB operon from genomic DNA isolated externally and by testing for the presence of the 16S rRNA gene of strain VS in those cultures.

For PCR-amplification of vcrAB operon from groundwater samples, total DNA from sediment material of 2 liters of groundwater samples was isolated with the UltraClean™ Soil DNA Isolation Kit (Mo Bio Laboratories, Inc.). The following primer pair was used: (SEQ ID NO:16) 5'-CTATGAAG-GCCCTCCAGATGC-3' and (SEQ ID NO:17) 5'-GTAA-CAGCCCCAATATGCAAGTA-3'.

Reverse-Transcriptase PCR (RT-PCR). Total RNA was prepared from cells in mid-log phase by a combination of TRIzol®-extraction (Invitrogen) and RNA clean-up with the RNeasy Mini Kit (Qiagen). DNA was removed from the RNA by three treatments with RNase-free DNase I (Qiagen). cDNA was synthesized from 0.2 to 0.8 µg RNA and 2 µmol of specific primer with SuperScript II RNAase H-Reverse Transcriptase (Invitrogen) as described by the supplier. The PCR amplification mixtures contained 6 µl cDNA, 200 nM of each primer, 200 µM dNTP, 1 U Taq Polymerase in PCR-buffer with 1.5 mM MgCl$_2$. For amplification of parts of vcrA, vcrB, vcrC, and intergenic regions of vcrA and vcrB, and vcrB and vcrC, five sets of primers were chosen for RT-PCR: (SEQ ID NO:18) vcrAf (5'-TGC TGG TGG CGT TGG TGC TCT-3') and (SEQ ID NO:19) vcrAr (5'-TGC CCG TCA AAA GTG GTA AAG-3'); (SEQ ID NO:20) vcrBf (5'-CTT GGC ATA TTG GGG CTG TTA C-3') and (SEQ ID NO:21) vcrBr (5'-ATT TGT CTA CCC TGC GTC TTA CTG-3'); (SEQ ID NO:22) vcrCf (5'-GTG GCC CTC TTA CGG TTG TT-3') and (SEQ ID NO:23) vcrCr (5'-CTAAGTGGCGAGAAA-GAATAATG-3'); (SEQ ID NO:24) vcrABf (5'-AAA ATA GTAAA AGG TGT TGT TGC-3') and (SEQ ID NO:25) vcrABr (5'-TAT TTG TCT ACC CTG CGT CTT A-3'); (SEQ ID NO:26) vcrBCf (5'-TGC GGC AAG ATC AGT AAG ACG-3') and (SEQ ID NO:27) vcrBCr (5'-GTA AGA GGG CCA CCA TAA CCA TAG-3'). PCR-parameters were as follows: 3 min at 92° C., 30 cycles of 0.45 min at 94° C., 1 min at 55° C. for the primer pairs vcrAf/vcrAr, vcrBf/vcrBr, vcrCf/vcrCr, and vcrBCf/vcrBCr, and at 50° C. for primer pair vcrABf/vcrABr, 1 min at 72° C., followed by 7 min at 72° C.

To determine the region of the transcriptional start site of vcrABC, the following primer pairs were used: (SEQ ID NO:28) vcrT1f (5'-TAT CTT TGC GTA TTT TGT GC-3') and (SEQ ID NO:29) vcrT1r (5'-GCC CGC TGA TCC CCT CTC-3'); (SEQ ID NO:30) vcrT2f (5'-TTG TAC TGA GGA AAC GCT TAT GG-3') and (SEQ ID NO:31) vcrT2r (5'-GCC CGC TGA TCC CCT CTC C-3'); (SEQ ID NO:32) vcrT3f (5'-CTT ATG GAT ATT TGG CGT TCA GGA-3') and (SEQ ID NO:33) vcrT3r (5'-AAT TCG CTT CTT TTG CTC TTC ACC-3'). PCR-parameters were essentially as above with an annealing temperature of 51° C.

Computer analysis. The nucleotide and amino acid sequences were analyzed using the DNAStar software package (DNASTAR, Madison, Wis.), as well as Simple Modular Architecture Research Tool SMART. Preliminary sequence data was obtained from The Institute for Genomic Research website and from the Joint Genome Institute.

Nucleotide accession number. All sequence data have been deposited in the GenBank database under accession no. AY322364.

Results

Cultivation of *Dehalococcoides* sp. strain VS. Anaerobic dehalogenation of VC was studied with a mixed bacterial culture (Victoria culture) comprised of greater than 99% of small cocci. The culture was grown in reduced mineral medium with VC or 1,1-DCE as electron acceptor, $H_2$ as electron donor, and acetate as a carbon source. An axenic culture of those small cocci was obtained, and its 16S rRNA gene sequence was found to be identical to that of the previously described *Dehalococcoides*-like bacterium VS. The mixed culture contained low numbers of three morphologically different types of organisms. These microorganisms were rapidly enriched for with either pyruvate or vanillate instead of VC as catabolic substrate. After four consecutive transfers (1%, v/v) in the presence of pyruvate or vanillate, these cultures had lost the ability to reduce VC and the small cocci could not be detected microscopically.

Partial purification and characterization of VC reductase. Our previous work had shown that the VC-reductive dehalogenating activity of the mixed culture was associated with the bacterial membrane fraction. For purification of VC-reductase, the highly enriched mixed culture was grown for 2 months in 20 l medium containing either VC or 1,1-DCE as electron acceptor and $H_2$ as an electron donor. Cell-free extract was prepared anoxically, and VC-reductive dehalogenating activity was solubilized from membranes in the presence of 2 mM CHAPS. The VC-reductase was partially purified about 4 fold to an apparent electrophoretic homogeneity of 50% by means of anion exchange chromatography and gel filtration (Table 1, FIG. 1). A single peak of VC-reductase activity was obtained at both chromatographic steps, suggesting that only one such enzyme was present in the culture.

TABLE 1

Purification scheme for VC reductive dehalogenase of *Dehaloccoides* strain VS

| Step | Protein (mg) | Activity[a] (mU) | Sp act (mU/mg protein) | Yield (%) | Purification factor |
|---|---|---|---|---|---|
| Cell-free extract | 40.5 | 8910 | 220 | 100 | |
| Membrane fraction | 16.2 | 5612 | 346 | 63 | 1.5 |
| Solubilized membrane fraction | 9.9 | 3047 | 308 | 34 | 1.4 |
| Anionic exchange chromotagraphy | 0.9 | 607 | 638 | 7 | 2.9 |
| Gelfiltration | 0.5 | 449 | 990 | 5 | 4.5 |

[a]Activity was monitored as described in Materials and Methods by gas chromatography with reduced methyl viologen as electron donor, and given activities are means of at least three independent measurements. One milli unit (mU) activity is defined as the rate of reduction of one nmol VC per minute.

However, the activity eluted during gelfiltration as a relatively broad peak, which was likely due to aggregation and/or micell formation of the detergent. During the anion exchange chromatography step, a high percentage (up to 90%) of the enzyme activity was irreversibly lost. Slightly better recovery of the activity was achieved with the pH of the elution buffer adjusted to pH 9.6 from 7.4, or 8.5, respectively. Addition of glycerol (20%) to the buffer or varying the detergent concentration (0.5 to 10 mM) did not increase the recovery of activity. Attempts to further purify VC-reductase with additional chromatographic steps (sequential anion exchange chromatography at different pH-values, hydrophobic interaction chromatography, hydroxyapatite, native- and blue native gel electrophoresis) were unsuccessful. In those latter cases, recovery of activity was essentially zero. Therefore, low yields after chromatographic steps in combination with low available biomass at the onset impeded purification of the protein to homogeneity. After gel filtration, protein fractions with VC-reductase activity displayed two major bands on SDS-PAGE gels, corresponding to an apparent molecular mass of 62 kDa and 45 kDa (FIG. 1). These two peptides were estimated to comprise 95% of the total protein in active fractions. Minor peptide bands of 30, 34, 76, 107, 140 and 175 kDa were also present. However, the bands at 30, 34, 76, 140 and 175 kDa were not detectable in all FPLC-fractions where VC-reductase activity was found.

Active protein fractions obtained after gel filtration catalyzed the reduction of VC (350 nmol min$^{-1}$ [mg protein]$^{-1}$) and all three DCE-isomers at high rates (350-390 nmol min$^{-1}$ [mg protein]$^{-1}$) with reduced methyl viologen as electron donor. The DCE isomers were first dehalogenated to VC, which was then further reduced to ethene. Reduction of TCE to cDCE was very slow and occurred at only 5% of the reduction rate for cDCE to VC. PCE was not transformed during the course of the enzyme assay (2 h). The reduction rate of VC was not affected in the presence of saturating concentrations of PCE or TCE. Thus, the enriched enzyme has preferred substrate specificity to VC and DCEs over TCE and PCE and was therefore designated as VC-reductase. The VC reductase activity was sensitive towards exposure to air with an activity half-life 5±3 min.

The N-terminal amino acid sequences of the two major peptide bands of 62 and 45 kDa as well as of the minor peptide band of 107 kDa were obtained. Furthermore, internal peptides of the 62 kDa band were obtained after a tryptic digest of the excised band. The amino acid sequence of the N-terminus of the 62 kDa peptide (SEQ ID NO:34) (EANSTKDQPW-YVKHREHFDP) was found to be similar to a 20 amino acid region of the N-terminus of TceA from *D. ethenogenes*. The sequence run showed no indication of background protein contamination. Three internal peptide fractions obtained after tryptic digestion of the 62 kDa peptide band were sequenced.

Two of those fractions appeared to be homogenous (SEQ ID NO:35) [peptide1: VYEGPPDA(P)FT(S/T) and (SEQ ID NO:36) peptide2: VGTLVQMF(L); ambiguous amino acid residues in parenthesis]. The third fraction contained two different peptides (SEQ ID NO:37) (peptide3: DAL-FYAVTQPFPG and (SEQ ID NO:38) peptide4: ESIXT-FTLP) of roughly equal abundance. All four sequences were found to have moderate identity (25-33%) with internal sequences of TceA.

The N-terminus of the 45 kDa peptide (SEQ ID NO:39) (AVREQVYGFFIPSVTLIGIG) was nearly identical to N-termini of some alcohol dehydrogenases. A BLASTP search in the deduced proteome of *D. ethenogenes* using the complete sequence of the alcohol dehydrogenase with the most similar N-terminus (accession number ZP_00128696) revealed a putative alcohol dehydrogenase gene located about 30 kb distant from tceAB. Interestingly, this 30 kb region contains almost exclusively phage-related genes and genes involved in DNA-recombination. The N-terminus of the 107 kDa peptide (SEQ ID NO:40) [ANQD(W)SKISLPGSGATG (G/A)YV] was highly similar (90% identity) to a amino acid sequence in the N-terminal region of a deduced protein of *D. ethenogenes*. This protein of a predicted molecular mass of 106 kDa showed no significant similarities to any other protein in the databases. Based on the abundance of the 62 kDa peptide in active protein fractions, the molecular similarity of this protein with other known reductive dehalogenases, as well as the absence of any other obvious candidate protein, we concluded that the 62 kDa peptide constitutes the catalytically active subunit of the VC-reductase.

Cloning of the genes encoding VC-reductase. Degenerate oligonucleotide primers were designed from the N-terminal amino acid sequence and one internal sequence of the 62 kDa peptide (see Material and Methods). PCR-amplification with those primers yielded a single 292 bp product, which, after sequencing, was found to be comprised of a single open reading frame (orf). The predicted amino acid sequence of this orf included the amino acid sequences of the N-terminus as well as those of peptide1 and peptide3 of the 62 kDa peptide.

Figure 2:
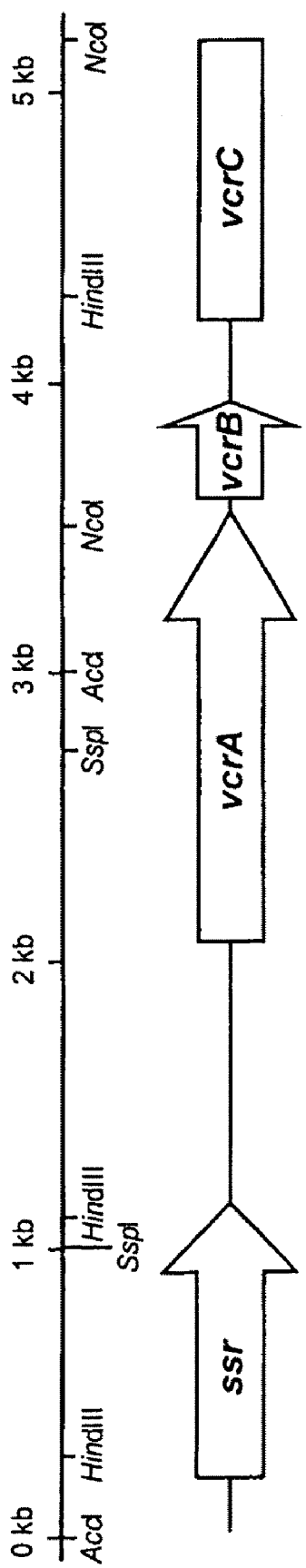
FIG. 2. Physical map of the vcr gene locus in *Dehalococcoides* sp. strain VS. The location and direction of open reading frames are indicated by arrows. Relevant restriction enzyme recognition sites are shown.

A probe generated from the 292 bp fragment was found in Southern blot analyzes to hybridize to a 1.6 kb SspI fragment, a 2.8 kb AccI fragment and a 2.8 kb HindIII fragment of restriction enzyme-digested genomic DNA of the mixed culture. The flanking DNA regions of the 292 bp product were subsequently amplified by several inverse PCR reactions using circularized SspI-, AccI-, HindIII-, and NcoI-digested genomic DNA as templates. The respective PCR-products were sequenced, and the four sequences were assembled into a 5.1-kb contig revealing four orfs (FIG. 2). The N-terminus and all 4 internal peptide sequences of the 62 kDa peptide were present in one orf, designated vcrA (for vinyl chloride reductase). The deduced VcrA sequence, however, contained an isoleucine at position 330 instead of the (ambiguous) leucine as indicated by the peptide2 sequence. A second orf, designated vcrB, was found immediately downstream of vcrA (FIG. 2). An orf that started 228 bp downstream of vcrB was found and designated vcrC. One additional orf upstream of vcrA was identified and designated ssr (for site-specific recombinase, see below).

Computational analysis of vcrA. The vcrA gene is 1560 bp in length and predicted to encode a polypeptide, VcrA, of 519 amino acids with a calculated molecular mass of 57,506 Da. The GC content of vcrA (44.6%) is similar to the GC content of the *D. ethenogenes* genome (48.9%) and the average GC content of the putative dehalogenase genes (48.3%) in this organism. A putative ribosome binding site and a sigma70-type promoter sequence (see below) were found upstream of the predicted start codon of vcrA. The N-terminal amino acid sequence of the partially purified vinyl chloride reductase matches amino acid residues at positions 44 to 63, respectively, of VcrA, consistent with the predicted polypeptide containing a leader sequence, which is cleaved off, leaving a mature polypeptide of 476 amino acids with a calculated molecular mass of 53,115 Da.

The proposed leader sequence containing a twin-arginine motif (Tat-motif) is predicted by motif-search using SMART, and is similar to those found in other reductive dehalogenases (14, 16, 23, 33, 35). Two motifs for iron-sulfur clusters were identified at positions 400-411 and 444-456. Both motifs are similar to the ferredoxin-type 4Fe4S-cluster (Cx2Cx2Cx3CP); here with the variations that the first motif contains a valine after the fourth cysteine instead of the canonical proline, and the second motif displays three amino acids between the first two cysteines instead of two as in the consensus sequence.

Figure 3:
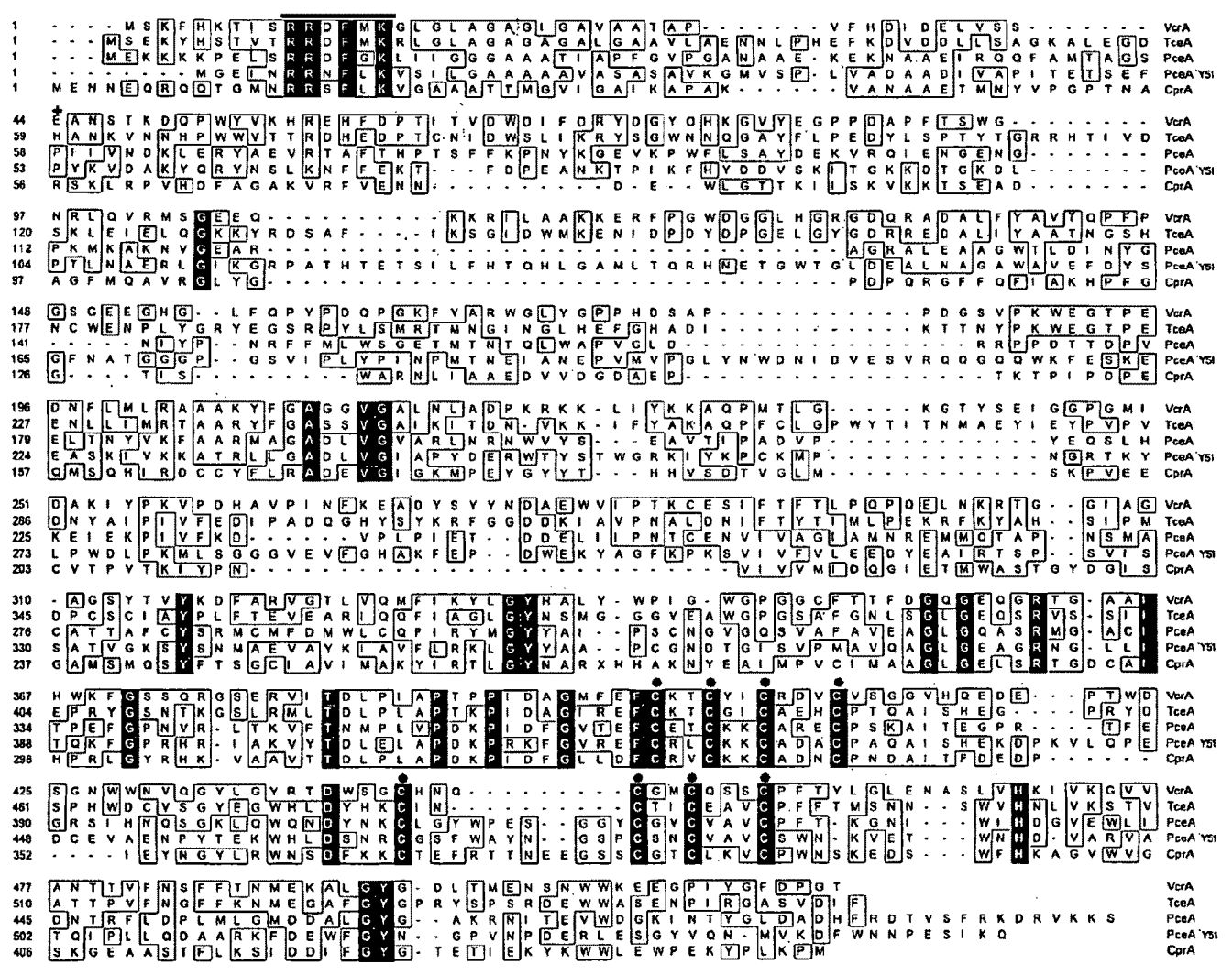

As for all other reductive dehalogenases, the described binding motif for corrinoids (DXHX2G) found in various corrinoid-containing enzymes (12) is absent in VcrA. The sequence of VcrA was aligned with those of described reductive dehalogenases (FIG. 3), as well as with putative dehalogenases identified in the genomes of *D. ethenogenes* and *Desulfitobacterium frappieri*. Closest similarity (36% identity) was with TceA from *D. ethenogenes*.

Identities with PCE dehalogenases from *Sulfurospirillum* [formerly *Dehalospirillum*] *multivorans* (PceA-Sm), *Dehalobacter restrictus* (PceA-Dr), and *Desulfitobacterium* sp. strain Y51 (PceA-Y51), and ortho-chlorophenol reductive dehalogenase from *Desulfitobacterium dehalogenans* (CprA) were between 14 and 19%.

VcrA was more identical to the putative dehalogenases from *D. ethenogenes* (up to 34% identity) than to that of *Ds. hafniense* (up to 23% identity). In addition to the leader sequence and the C-terminal two iron-sulfur cluster motifs, several highly conserved amino acid residues, including a conserved histidine, H469, is present in VcrA and all other reductive dehalogenases. Furthermore, the sequence in VcrA ranging from amino acid 198 to 215 displays strong similarity to a region in TceA and all putative dehalogenases from *D. ethenogenes*.

Computational analysis of vcrB. vcrB, a gene of 282 bp, is located 41 bp downstream of vcrA and preceded by a putative ribosome binding site. The 94, predominantly hydrophobic amino acids account for a calculated molecular mass of 10,641 Da (VcrB). Sequence analysis of VcrB with Protean (DNAStar) and SMART predicted the presence of three transmembrane spanning regions (not shown). The predicted VcrB sequence shows some identity to proposed membrane anchors (B-proteins) for described as well as putative reductive dehalogenases. The most similar sequence to VcrB was TceB with 43% identity. Canonical binding motifs for redox-active cofactors, i.e, iron-sulfur cluster, heme, NAD/FAD, or flavin were not detected in VcrB.

Computational analysis of vcrC. The presumed start codon of vcrC is 228 bp downstream of vcrB. No transcriptional stop codon for vcrC was found in the DNA fragment analyzed. The partial vcrC gene translates into a protein, VcrC, of at least 305 amino acids with a calculated molecular mass of at least 33,363 Da. Four potential membrane-spanning helices can be predicted to occur in VcrC. The amino acid sequence of VcrC displays some similarity (25% identity) to CprC from *D. dehalogenans*. CprC was postulated to function as a NosR/NirI-type transcriptional regulator in ortho-chlorophenol respiration. Four orfs similar to VcrC were also found in the deduced proteome of *D. ethenogenes* (38-47% identity). Two of those are located at loci next to genes encoding putative dehalogenases. The other two orfs are located directly downstream to homologs of tatB and tatC, components of the translocation apparatus for proteins carrying the Tat-motif.

Figure 4:
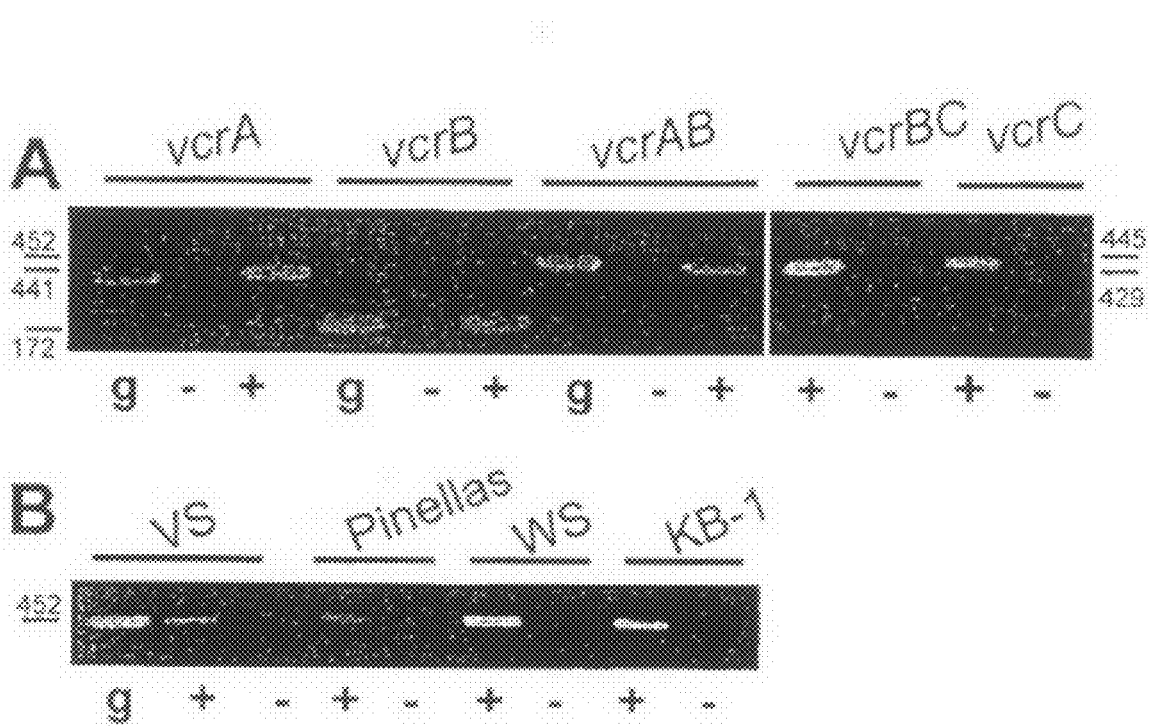
FIG. 4. Reverse Transcriptase-PCR (RT-PCR) analysis of vcrA, vcrB, and vcrC in *Dehalococcoides* sp. strain VS. (A) Transcriptional organization of vcrA, vcrB and vcrC as an operon in strain VS. Agarose gel electrophoresis of RT-PCR assays with primers targeting vcrA, vcrB, and vcrC, and intergenic regions of vcrA and vcrB, and vcrB and vcrC, respectively. (B) Transcription of vcrA in strain VS, and in the mixed cultures Pinellas, WS, and KB-1. "g" stands for genomic DNA as template, "+" for assays with RNA as template and conducted with Reverse Transcriptase, and "−" for assays with RNA as template conducted without Reverse Transcriptase. Sizes of products are indicated and were as predicted (for vcrA 441 bp, for vcrB 172 bp, for vcrAB 452 bp, for vcrBC 429 bp, for vcBC 445 bp). Absolute positions of used primers, vcrAf, 2691-2711; vcrAr, 3111-3131; vcrBf, 3773-3793; vcrBr, 3921-3944; vcrCf, 4346-4365; vcrCr, 4767-4790; vcrABf, 3472-3494; vcrABr, 3924-3945; vcrBCf, 3910-3930; vcrBCr, 4335-4358.
Figure 5:
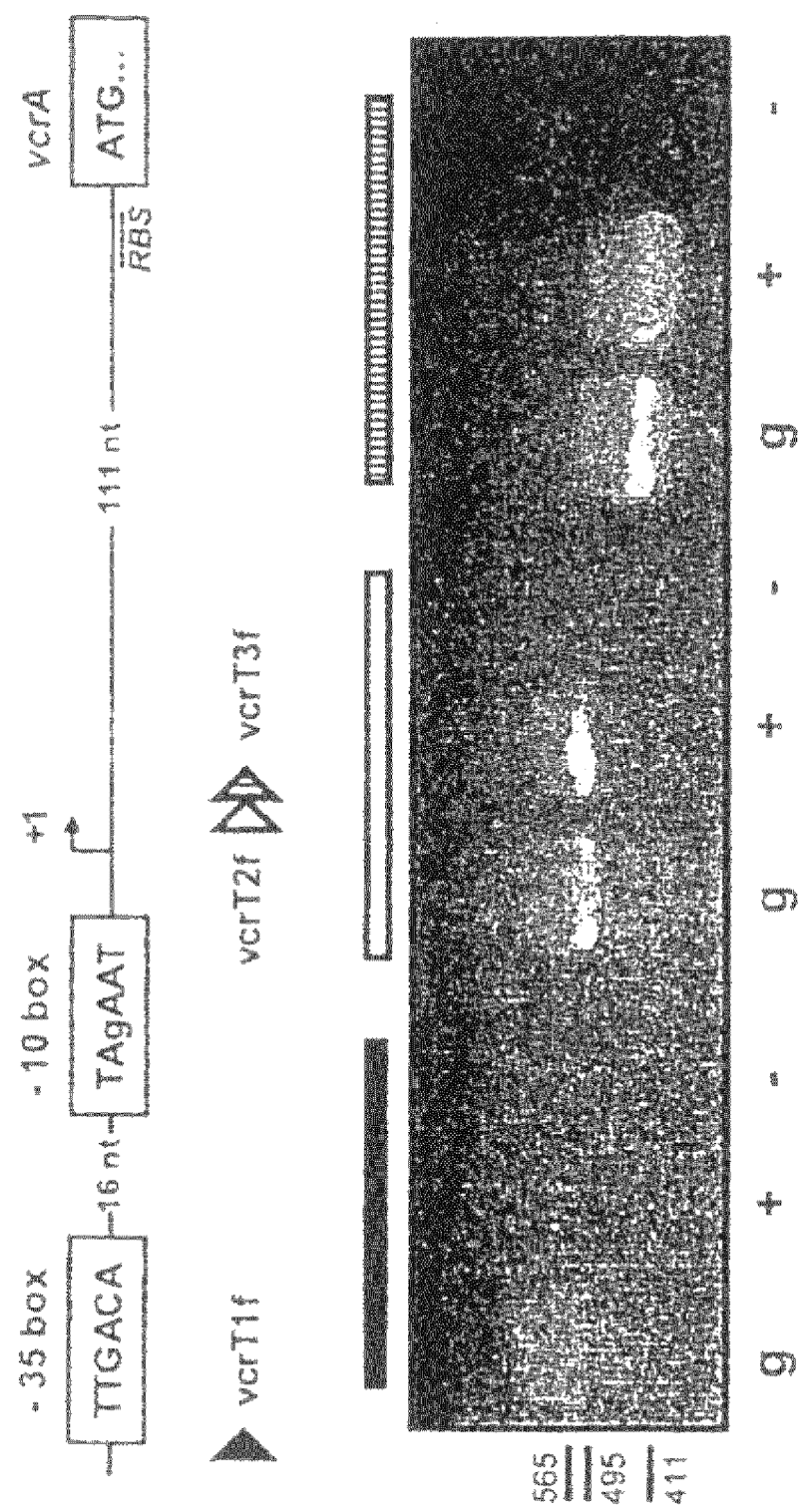
FIG. 5. Transcriptional start and promoter region of vcrABC. A) Schematic diagram of nucleotide region upstream of vcrA in *Dehalococcoides* sp. strain VS and B) Reverse Transcriptase-PCR (RT-PCR) analysis of region of transcriptional start site. The putative −10 and −35 regions, and the putative translational start site of vcrA are boxed, the putative transcriptional start site is indicated by a bend arrow, and the position of a putative ribosome binding site (RBS) is underlined. The positions of forward primers used in RT-PCR are indicated by shaded triangles (position of reverse primers not shown), and corresponding PCR products are indicated by shaded horizontal bars (see text for details). Absolute nucleotide positions: vcrT1f, 1904-1923; vcrT2f, 1974-1996; vcrT3f, 1990-2013; −35 region, 1926-1931; −10 region, 1948-1953; predicted transcription initiation site, 1960; translational start site, 2065. "g" stands for genomic DNA as template, "+" for assays with RNA as template and conducted with Reverse Transcriptase, and "−" for assays with RNA as template conducted without Reverse Transcriptase. Sizes of products are indicated and were as expected (for vcrT1 565 bp, for vcrT2 495 bp, for vcrT3 411 bp).

Transcriptional organization of vcrA, vcrB, and vcrC. Transcription of vcrA, vcrB, and vcrC was investigated in a series of reverse transcriptase experiments. Reverse Transcriptase-PCR was performed on RNA isolated from VC-grown cells. RT-PCR assays with primer pairs designed to amplify internal fragments of vcrA, vcrB, and vcrC, respectively, yielded products of the expected sizes (FIG. 4). PCR-products were also obtained for the intergenic regions of vcrA and vcrB as well as of vcrB and vcrC. The RNA-specific recovery of these products demonstrates that vcrA, vcrB, and vcrC are expressed as a polycistronic unit during growth on VC. Two DNA sequences upstream of vcrA were nearly identical to the −10 and −35 regions of an *E. coli* □70-promoter (FIG. 5). RT-PCR assays were conducted to determine whether the transcriptional start site of the vcrABC operon is located downstream of that s70-promoter consensus sequence. PCR products were obtained only with forward primers matching regions downstream but not upstream of the putative transcriptional start site. These results map the transcriptional start of the vcr operon to a region containing a s70-type promoter sequence.

DNA region upstream of vcr operon. Upstream (850 bp) of the start-codon of vcrA, an open reading frame, ssr, of 972 bp was identified (FIG. 2). It translates into a predicted protein of 324 amino acid residues with a calculated mass of 36,553 Da. A BLASTP search revealed low similarity (25-28% identity) to site-specific recombinases of the resolvase family containing a Pin domain (28). A putative ribosome binding site was not identified immediately upstream of the start codon.

Presence of vcrAB homologs in other cultures containing *Dehalococcoides* spp. Degenerate PCR primers were designed and used to probe for the presence of the vcrA gene in three mixed cultures KB-1 (17), Pinellas (5), and WS. These cultures contain *Dehalococcoides*-like organisms that can grow by reductive dehalogenation of VC to ethene. PCR products of size of 1393 bp were obtained from genomic DNA of all three cultures. The products were cloned and sequenced, and found to be highly similar to the corresponding sequence of vcrA previously identified in *Dehalococcoides* sp strain VS. Additional primers were designed to amplify the complete vcrA and vcrB genes from those cultures. The thereby obtained nucleotide sequences showed high identities (>98%) to vcrAB of *Dehalococcoides* sp. strain VS, and the deduced amino acid sequences contained only a few conservative changes suggesting that they are true homologs. The expression of vcrA during growth of KB-1, Pinellas, and WS with VC electron acceptor was demonstrated by RT-PCR analysis (FIG. 4). *Dehalococcoides* strains 195, CBDB-1 and a culture containing strain FL-2 were examined for the presence of a vcrA homolog by PCR. None of these cultures have been reported to grow by reductive dehalogenation of VC. With the primer set used, no PCR product was obtained with genomic DNA from those cultures as template.

Detection of a vcrAB homolog in contaminated groundwater samples. The strong correlation of the presence of a vcrA homolog with reductive VC dehalogenation, as observed in the above described dehalogenating culture, suggested that the vcrAB sequence could be useful as a molecular probe for testing for in situ VC-reduction potential at contaminated field sites. Such molecular probes could prove valuable when evaluating, monitoring or predicting complete removal of chlorinated ethenes from groundwater in field scale bioremediation projects. Therefore, we queried for the presence of the vcrAB genes groundwater samples from a chlorinated ethene-contaminated aquifer at Moffett Field, Calif., where complete reductive dehalogenation to ethene was achieved through biostimulation of indigenous microorganism. DNA extracted from groundwater wells exhibiting VC reduction as well as from areas where VC dehalogenation did not occur was used as template in PCR experiments using the primers described above. PCR products were obtained only from groundwater samples undergoing VC reduction to ethene. One of the PCR-products was sequenced, and its vcrAB genes were found to be nearly identical (>98%) to those obtained from *Dehalococcoides* sp. strain VS.

Reductive dehalogenation of VC has long been considered as the most critical step for complete anaerobic removal of PCE/TCE from groundwater and contaminated soils, but the molecular features of reductive VC dehalogenation have been largely unknown. Here, for the first time, a VC-reductive dehalogenase was partially purified, and its encoding genes, vcrAB, were identified and characterized. Furthermore, a strong correlation between the presence of vcrAB in other cultures and catabolic reductive VC dehalogenation was found. A PCR assay testing for the in situ presence of vcrAB was successfully developed and used on groundwater samples from a site contaminated with chlorinated ethenes. The data suggest that the vcrAB genes identified here may be widely distributed, be of relevance for in situ VC-reductive dehalogenation, and be a useful target for molecular probing of samples from chlorinated ethene-contaminated sites.

The VC reductive dehalogenase was partially purified from a highly enriched culture of *Dehalococcoides* sp. strain VS. The partially purified enzyme reduced VC and the three DCE isomers with similar high rates. TCE was reduced with significantly lower activity, and PCE was not converted. This is in agreement with our earlier results on chloroethene reduction rates in cell-free extract of the parent mixed culture. As with most other chloroethene reductive dehalogenases, VC reductive dehalogenase was associated with the membrane fraction, which is consistent with this enzyme being involved in energy conservation during VC reduction to ethene. Analysis of the identified genes encoding VC reductase revealed that this enzyme is a novel member of the family of corrinoid/iron-sulfur cluster containing reductive dehalogenases. The hydrophobic VcrB protein presumably acts as a membrane anchor for the catalytic subunit of VC reductase. The VcrC protein likely plays a role in regulation of transcription of the vcr operon. The precise function, however, remains to be elucidated.

Chlorinated ethenes have been assumed to be introduced into the environment essentially due to human activities within the last decades, although this has been questioned recently for VC. Interestingly, the vcr operon is downstream of a putative site-specific recombinase gene. It is noteworthy that also tceAB in *D. ethenogenes* 195 (The Institute for GenomicResearch, Bethesda, Md.) and pceAB in *Desulfitobacterium* sp. strain Y51 are located in close proximity to putative transposase genes. While the evolutionary origin of those reductive dehalogenases remains unknown, it is tempting to speculate that the parent genes might have encoded enzymes catalyzing the reductive dehalogenation of naturally occurring chlorinated compounds, and that through recent gene duplication/transposition, mutation and selection the substrate specificity towards the anthropogenic chlorinated ethenes was acquired.

So far, only microorganisms affiliated with the *Dehalococcoides*-group are known to be able to grow on VC. Because not all *Dehalococcoides* strains use VC as catabolic electron acceptors, simply demonstrating the presence of members of the *Dehalococcoides*-group (based on phylogenetic analysis) at chlorinated ethene-contaminated sites is insufficient for predicting growth-linked, hence rapid, VC degradation. The occurrence and expression of homologs of vcrAB in cultures containing *Dehalococcoides*-like organisms growing on VC, but not in members of the *Dehalococcoides*-group which are unable to grow by reductive dehalogenation of VC, strongly suggest that the vcrAB gene sequence can be used to determine the presence of VC-respiring bacteria at contaminated field sites. Indeed, during this study the presence of vcrAB in a contaminated aquifer undergoing complete reductive dehalogenation of chlorinated ethene to ethene was demonstrated. This methodology could allow for better assessing the potential for biological degradation of chlorinated ethenes at numerous contaminated field sites, and, in combination with bioaugmentation, may become a powerful tool for the cleanup of chlorinated solvents.

Example 2

Comparative Evaluation of Chloroethene Dechlorination to Ethene by *Dehalococcoides*-Like Microorganisms Tetrachloroethene (PCE) and trichloroethene (TCE) are among the most common organic groundwater contaminants. Under anaerobic conditions, they may be converted biologically through reductive dehalogenation to cis-1,2-dichloroethene (DCE) (trans-dichloroethene or 1,1-dichloroethene may also be formed, 1), vinyl chloride (VC), and then ethene. Prior to the present invention, no microorganism had been isolated that can grow through every step in the reductive dechlorination of PCE or TCE to ethene. Several phylogenetically different bacteria have been identified with the ability to convert PCE and TCE to DCE, but the reduction of DCE to VC and ethene appears to be carried out for the most part by organisms of the genus *Dehalococcoides*.

The first such organism identified, *Dehalococcoides ethenogenes* strain 195, obtains energy for growth from reduction of PCE, TCE, and DCE to VC. It can convert VC to ethene, but does so only cometabolically. In contrast, *Dehalococcoides* species strain VS, and *Dehalococcoides* isolate BAV1 can derive energy from both DCE and VC reduction to ethene, although *Dehalococcoides* isolate BAV1 uses TCE and PCE only cometabolically.

In the field, complete transformation to ethene, the desired endpoint, often does not occur naturally because of insufficiency in required electron donor, reaction kinetics, the absence of necessary dehalogenating bacteria, or other environmental factors. Engineering efforts to enhance complete microbial reductive dehalogenation at contaminated sites generally involve adding electron donor. Mixed cultures, such as Pinellas and KB-1, containing *Dehalococcoides*-like strains, have been successfully used in field bioaugmentation demonstrations to bring about complete dehalogenation to ethene. Other cultures with the ability to reductively dechlorinate VC to ethene rapidly may be found. The question of which culture is best for use arises when considering bioaugmentation. We present here a method that can be used to make such a judgment together with a comparative study of the utilization of VC, DCE, TCE, and PCE by four of the above mentioned cultures or strains.

Materials and Methods

Chemicals. Liquid cis-1,2-dichloroethene (97% Aldrich Chem. Co., Milwaukee, Wis.), trichloroethene (99+% Aldrich Chem. Co.), tetrachloroethene (99.9+% Sigma-Aldrich) and gaseous vinyl chloride (99.5%, Fluka, Switzerland) were used neat, to prepare stock solutions and analytical standards. In addition, ethene (1000 PPM and 100 PPM, Scott Specialty Gases, Alltech Associates) and vinyl chloride (1000 PPM and 10 PPM, Scott Specialty Gases, Alltech Associates) were used as analytical standards, benzoate (sodium salt, 99%, Aldrich Chem. Co.) as a substrate, and sodium sulfide (Aldrich Chem. Co.) as a reducing agent.

Analytical methods. Analyses of ethene, VC, DCE, TCE and PCE were performed with a temperature program (40 to 220° C.) using a Hewlett-Packard model 5890 Series II gas chromatograph equipped with a flame ionization detector (Hewlett-Packard) and a GS-Q fused-silica capillary column (length, 30 m; inside diameter, 0.53 mm; J&W Scientific). A reduction gas analyzer (Trace Analytical, Inc., Menlo Park, Calif.) was used to measure hydrogen. Solution concentrations and total mass were calculated using Henry's Law Constants.

Stock cultures. The Victoria mixed culture, containing strain VS, was maintained in a closed continuously stirred tank reactor (CSTR) as previously described. A VC enrichment of this culture, maintained over 5 years, was also used in these investigations. Liquid cultures of the three other cultures evaluated (Pinellas, KB-1/VC, and *Dehalococcoides ethenogenes* strain 195) were kept in anaerobic bottles, stored in an anaerobic chamber (10% $H_2$, 10% $CO_2$, 80% $N_2$). The bottles were amended with TCE (1-3 µL neat liquid), VC (250 µL gas), and PCE (1-3 µL neat liquid) being added to each, respectively, approximately every two weeks.

Batch studies. For the experimental portion of this research, two studies were undertaken, one a comparative VC growth study, and the other a comparative growth and substrate utilization study with different chlorinated ethenes. These studies compared the dechlorination abilities of *Dehalococcoides ethenogenes* strain 195 and the *Dehalococcoides*-like microorganisms in the three mixed cultures (Victoria, KB-1/VC, and Pinellas).

For the first study, a VC enriched inoculum was first developed for each of the three mixed cultures. Here, bottles (120 mL) were filled with 60 mL of anaerobic media in an anaerobic chamber as previously described, and inoculated with 200 µL of each stock culture. Gaseous VC (99.5%) was added with a gas tight syringe (200 µL). The cultures were then moved to a shaker (60-80 rpm) in an anaerobic chamber (20±2° C.). Immediately after 5 µmol of ethene was formed in a bottle, 200 µL of the culture was transferred to fresh media (60 mL), in triplicate, and VC was again added (200 µL). The inoculum for the growth study was that formed after exactly 4 µmol of ethene was produced following this second transfer. To compare growth rates on VC, a range in concentration of each inocula (0.1, 0.3, 1, 3, 9 mL) was transferred to fresh media (as above) to result in a liquid volume of 60 mL, and gaseous VC (200 µL) was added to each. An abiotic control with media and VC was included in all batch studies to demonstrate the cultures were required for dechlorination. Hydrogen served as the electron donor and was non-limiting (>3%) in all studies. Headspace samples were periodically removed by syringe (250 µL) for chlorinated ethene analyses.

The purpose of the second study was to compare dechlorination rates of PCE, TCE and DCE between the three different cultures that grew on VC (Victoria, KB-1/VC and Pinellas). The development of inocula here was performed with VC, just as in the first study. For the growth and substrate utilization experiments, triplicate bottles were set up for each culture containing 1 mL of inoculum and either neat PCE (0.4 µL), neat TCE (0.3 µL), saturated DCE solution (34 µL) or gaseous VC (200 µL). To further investigate TCE removal, bottles (120 mL) were filled with 20 mL of a highly enriched culture of strain VS made from the Victoria culture. Duplicate bottles were supplied with gaseous VC (50 µL on day 0, then 150 µL on day 3) or TCE (0.4 µL neat liquid). Dechlorination was followed until all VC or TCE was converted to ethene (day 12). The change in strain VS concentration during VC and TCE utilization was then determined both by competitive PCR and by an activity procedure evaluated previously for strain VS. In the activity procedure a non-growth limiting concentration of VC (150 µL) along with excess hydrogen is added to a culture and the initial dechlorination rate is measured (over <1 day). A good estimate of strain VS concentration can then be obtained using the previously determined strain VS maximum VC utilization rate ($7.8 \times 10^{-10}$ µmol Cl$^-$ (cell·d)$^{-1}$). The increase in strain VS concentration during TCE or VC utilization was determined with these two procedures on the culture before and after TCE and VC utilization.

Comparative dechlorination and growth kinetics. With mixed cultures, the concentration of organisms carrying out a particular reaction is generally unknown and difficult to determine. Thus, reaction rates with mixed cultures are generally reported in units that cannot be used for comparative purposes. For example, dechlorination rates have been reported in mass removal rate per microcosm or bottle, per unit liquid volume, per unit of total biomass or per unit of total protein. However, the approach described here allows us to make direct comparisons of basic dechlorination and growth kinetics between cultures. The main parameter used in this comparison is organism maximum growth rate, which is directly related to dechlorination kinetics. The maximum growth rate for each culture was determined from a least-squares model fit to experimental data. For this purpose, the dechlorination of TCE, DCE, and VC was modeled using Monod kinetics with competitive kinetics between the multiple electron acceptors involved in dechlorination (for the case when electron donor is non-rate-limiting):

$$-\frac{dVC}{dt} = \frac{\frac{\mu_V}{Y}XVC}{VC+K_V 1+\frac{DCE}{K_{ID}}\frac{TCE}{K_{IT}}} \frac{\frac{\mu_D}{Y}XDCE}{DCE+K_D 1+\frac{VC}{K_{IV}}\frac{TCE}{K_{IT}}} \quad (1)$$

$$-\frac{dDCE}{dt} = \frac{\frac{\mu_D}{Y}XDCE}{DCE+K_D 1+\frac{VC}{K_{IV}}\frac{TCE}{K_{IT}}} \frac{\frac{\mu_T}{Y}XTCE}{TCE+K_T 1+\frac{VC}{K_{IV}}\frac{DCE}{K_{ID}}} \quad (2)$$

$$-\frac{dTCE}{dt} = \frac{\frac{T}{Y}XTCE}{TCE+K_T 1+\frac{VC}{K_{IV}}\frac{DCE}{K_{ID}}} \quad (3)$$

$$\mu = \frac{\mu_V VC}{VC+K_V 1+\frac{DCE}{K_{ID}}\frac{TCE}{K_{IT}}} \quad (4)$$

$$\frac{\mu_D DCE}{DCE+K_D 1+\frac{VC}{K_{IV}}\frac{TCE}{K_{IT}}} \frac{\mu_T TCE}{TCE+K_T 1+\frac{VC}{K_{IV}}\frac{DCE}{K_{ID}}} b$$

Here, $\mu_V$, $\mu_D$ and µT are the maximum growth rates (d$^{-1}$) on VC, DCE and TCE respectively, b is the cell decay rate (d$^{-1}$), X is the concentration (cells L$^{-1}$) of dechlorinating cells and Y is the yield (cells (µmol)$^{-1}$). VC, DCE and TCE are the solution concentrations (µM) of VC, DCE and TCE respectively. $K_V$, $K_D$ and $K_T$ are the half-velocity coefficients (µM) for VC, DCE and TCE. $K_{IV}$, $K_{ID}$ and $K_{IT}$ are the competitive coefficients (µM) for VC, DCE and TCE respectively. As summarized in Table 2 these coefficients for VC and DCE were determined previously, while the coefficients for TCE were determined as part of this study.

TABLE 2

| Coefficients | Units | DCE | VC |
| --- | --- | --- | --- |
| Half-velocity ($K_D$, $K_V$) | M | $3.3 \pm 2.2^a$ | $2.6 \pm 1.9^a$ |
| Competitive ($K_{ID}$, $K_{IV}$) | M | $3.6 \pm 1.1^b$ | $7.8 \pm 1.5^b$ |

[a]
[b]

Kinetic coefficients and growth rates, along with 95% confidence intervals, for the reductive dechlorination of DCE and VC developed previously with the Victoria culture and used in this study.

In order to determine the maximum growth rates from these equations from measured concentrations of TCE, DCE, and VC, values for Y, X, b, $K_i$, and $K_{ij}$ are needed, where i and j are designators for v, d, t and D, T, respectively. The values Y and X, in particular, are difficult to measure with mixed cultures. However, this difficulty can be surmounted with the batch technique used. The inoculum approach used resulted from growth of a very small seed concentration on a known amount of VC. The concentration of VC dehalogenating organisms in the inocula is thus equal to $YS_m/V_b$ where $S_m$ is the mass (µmol) of VC consumed and $V_i$ is the culture volume of the seed vessel. When x ml of this inocula is transferred to the 60 ml of media in the batch bottles, the concentration is reduced by the dilution factor, D, which here equals x/60. This gives an initial organism concentration, $X^o$, in the batch culture, which is related to the dilution used, $$X^o \frac{DYS_m}{V_i} \text{ or } \frac{X^o}{Y} \frac{DS_m}{V_i} \quad (5)$$

Organism growth rate is related to the change in organism concentration as follows:

$$\int \frac{dX/dt}{X}, \text{ or } \frac{dX}{Y}\frac{X}{Y} dt \quad (6)$$

In the numerical approach used here, the value X/Y in Eqs. 1 to 3 from one time step in the numerical model is increased by dX/Y as indicated in Eq. 6 for the next time step. In other words, $$X_k DS_m (1+\mu 1\Delta t)(1+\mu 2\Delta t) \ldots (1+\mu \kappa \Delta t)] \quad (7)$$

where $X_k$ is the microorganism concentration after k time steps. With the dilution procedure, the value on the right side of Eq. 7 is substituted into Eqs. 1 to 3, resulting in the cancellation of X and Y, so that neither need be known to solve the system of equations.

While the values of $\kappa_i$ is also an unknown, except for strain VS, this was relatively unimportant in the determination of maximum growth rates since the initial substrate concentrations used were well above this value so that growth rates were highly insensitive to $K_i$.

Modeling approach. The above procedure was utilized to compare VC, DCE and TCE maximum growth rates between the *Dehalococcoides* like-microorganisms in the three cultures (strain VS, KB-1/VC and Pinellas). Previously determined VC and DCE half-velocity and competitive coefficients were included in this modeling approach (Table 2). Also, a previously determined decay coefficient (0.05 d$^{-1}$) for cells growing under optimal conditions (non-limiting electron acceptor and donor) was included. This leaves the maximum growth rates on individual chlorinated ethenes ($\mu V$, $\mu D$, or $\mu T$) as the only fitting parameters, which were determined, together with the 95% confidence interval) using non-linear least-squares fit to the experimental data.

DNA isolation and competitive PCR. For the Victoria, Pinellas, and KB-1/VC genomic DNA was extracted (1 mL) from the inoculum used in the VC growth comparison study and also from cultures in the comparative substrate utilization study following complete TCE dechlorination. DNA was extracted using a DNeasy® tissue system (Qiagen Inc, Valencia, Calif.), following the manufacture's instructions (final volume 200 μL). DNA was extracted from the *D. ethenogenes* strain 195 culture following dechlorination of DCE. Competitive PCR was carried out, as previously described, on DNA extracted from the VC enrichment culture of strain VS following TCE and VC dechlorination (day 12), in order to determine cell concentration.

Amplification and cloning of 16S rRNA genes. PCR with forward primer DeF and reverse primer DeR, as previously described, was carried out on DNA extracted from all cultures. Aliquots of the PCR products were resolved by electrophoresis in 2% (wt/vol) agarose gel (Sigma) in TBE buffer, stained in ethidium bromide solution (5 μg/mL) for 20 min, followed by destaining in water for 40 min. The bands, visualized upon UV excitation, were found to be of the appropriate size with a 1-kb DNA ladder (Gibco). The remaining PCR products were cloned into *E. coli* with a TOPO TA Cloning® kit (Invitrogen Corporation, Carlsbad, Calif.) following the manufacturers instructions. Plasmids were extracted from the cloned cells using a QIAprep® 2miniprep system (Qiagen Inc) and the inserts were sequenced (Stanford University's Protein and Nucleic acid facility, PAN).

For DNA extracted from the KB-1/VC and Pinellas cultures (used for inoculum in the VC growth comparison study) partial sequences (1091-1320 base pairs) from nine clones each were obtained. For DNA extracted from *D. ethenogenes* strain 195 and for DNA extracted from the Victoria inoculum (used in the VC growth comparison study) partial sequences (ranging from 421-930 base pairs) from five clones each were obtained. For DNA extracted from cultures following TCE dechlorination, partial sequences (960-1140 base pairs) from four (Pinellas) or five (Victoria and KB-1/VC) clones each were obtained. The sequences were compared to known sequences using BLAST in GenBank and were analyzed with DNASTAR MegAlign software.

Results and Discussion

VC dechlorination. Dechlorinating microorganisms in the Victoria, KB-1/VC, and Pinellas cultures dechlorinated VC to ethene, forming 5 μmol of ethene in 18 days (Victoria and KB-1/VC) or 21 days (Pinellas) (FIG. 6). As expected of cells growing on VC, the initial dechlorination rate was low following inoculation and increased exponentially with time. Standard deviations from the second transfer (triplicate cultures), illustrate the level of reproducibility typical of these experiments (FIG. 6). *D. ethenogenes* strain 195 did not dechlorinate VC, indicating no growth on VC, but did dechlorinate DCE to VC (with no further reduction to ethene), as expected (FIG. 7).

The results of the VC-fed serial dilution study for each of the three mixed cultures are illustrated in FIG. 8. The μv values and 95% confidence intervals obtained by least-squares fitting of Eq. 4 to 7 to these results of the FIG. 8 results are summarized in Table 3.

TABLE 3

Maximum growth rates and 95% confidence intervals for reductive dehalogenation of TCE, DCE, and VC by three different mixed cultures and one highly enriched culture.

| Culture | Maximum Growth Rate (d$^{-1}$) | | |
|---|---|---|---|
| | $\mu_T$ | $\mu_D$ | $v$ |
| VS Mixed | 0.35 ± 0.07 | 0.46 ± 0.04 | 0.49 ± 0.02 |
| Highly enriched | 0.35 ± 0.13 | | |
| KB-1/VC | 0.33 ± 0.06 | 0.44 ± 0.02 | 0.42 ± 0.03 |
| Pinellas | 0.49 ± 0.03 | 0.43 ± 0.00 | 0.28 ± 0.01 |

The growth rates of the dehalogenators in the Victoria and KB-1/VC cultures are similar (0.49 and 0.42 d$^{-1}$, respectively), while that of the Pinellas culture is lower (0.28 d$^{-1}$). The value of 0.49 d$^{-1}$ compares with that of 0.4 d$^{-1}$ determined previously using the more traditional method of cell counting. The dilution method used here is believed to be more precise because of the normal errors in cell counting methods, especially with mixed cultures. In summary, evidence for growth of dehalogenating bacteria in these three cultures on VC provided by the current study includes the repeated transfer of VC dehalogenating microorganisms, the increased rate of VC consumption following each transfer, increased VC dechlorination in cultures with greater inocula, and their similarity in VC dechlorination kinetics.

DCE, TCE and PCE Dechlorination. In the second study, triplicates of each individual mixed culture grown on VC was supplied with DCE, TCE or PCE. Using the dilution procedure, the dehalogenation results from cultures fed DCE were used to determine the maximum growth rate on DCE alone ($\mu D$) using least-squares analysis and the values for $\mu_V$ from Table 3. The maximum growth rates found for growth on DCE alone ($\mu D$) are similar for the three mixed cultures (0.43 to 0.46 d$^{-1}$), and are also similar to that on VC by the Victoria and KB-1/VC cultures (0.42 to 0.49 d$^{-1}$) (FIG. 9). In agreement with this, recent research indicates that the purified VC-reductase from strain VS from the Victoria culture dehalogenates DCE and VC at similar rates.

FIG. 10 illustrates a representative model fit for TCE removal (Pinellas culture). An unexpected finding was that all three mixed cultures dehalogenated TCE. Since the half velocity ($K_T$), inhibition coefficient ($K_{IT}$), and maximum growth rate ($\mu_T$) for TCE were unknown, the three coefficients were used as fitting parameters along with previously determined values for μV and μD from Table 3 in a least-squares fit to the TCE utilization data. The maximum growth rate found for TCE utilization alone was again the same for the Victoria and KB-1/VC cultures (0.23 d$^{-1}$), but lower than that for the Pinellas culture (0.49 d$^{-1}$). Also of interest is that the half velocity and inhibition coefficients for TCE utilization by the three cultures (KT and KIT) are equal to each other and about the same for the three cultures varying between 8.6 and 10.5 (Table 4). The near equality between the half velocity and inhibition coefficients was found previously for DCE. With VC on the other hand, the inhibition coefficient is significantly higher than the half-velocity coefficient, the higher value meaning the presence of VC is less inhibitory to the dehalogenation of DCE and TCE.

TABLE 4

Half velocity and inhibition coefficients for reductive
dehalogenation of TCE by three different mixed cultures
and one highly-enriched culture.

| | Coefficient (μM) | |
|---|---|---|
| Culture | $K_T$ | $K_{IT}$ |
| VS Mixed | 9.0 ± 0.4 | 8.6 ± 0.4 |
| Highly enriched | 12.4 ± 0.6 | 6.8 ± 1.4 |
| KB-1/VC | 10.0 ± 2.0 | 10.0 ± 0.6 |
| Pinellas | 10.5 ± 0.7 | 10.5 ± 0.7 |

The rapid utilization of TCE by the cultures came somewhat as a surprise because the recently isolated, VC-respiring *Dehalococcoides* isolate BAV1 uses TCE only co-metabolically. This rapid utilization of TCE and the strong suggestion from the model that this utilization is coupled with growth ($\mu_T$ values of 0.35 to 0.49 d$^{-1}$) was further investigated using the VC enrichment of the Victoria culture. Here in a separate study using a highly enriched (>95% purity) strain VS culture developed from the Victoria culture, the separate utilization of TCE and VC was investigated. FIGS. 6 and 7 illustrate a comparison between experimental data and modeled results using Table 1 to 3 coefficients, except for $\mu_T$, $K_T$, and $K_{IT}$, which were determined using the dilution technique and the data in FIG. 11. The value for $\mu_T$ was found to match that found with the mixed Victoria culture (0.35 d$^{-1}$). The values for $K_T$, and $K_{IT}$ were similar (Table 3). Growth yields on both TCE and VC were determined using competitive PCR, resulting in values of 4.7±0.3×10$^8$ cell/μmol Cl$^-$ when grown on TCE and 5.2±0.4×10$^8$ cell/μmol Cl$^-$ when grown on VC. A third method to confirm growth occurred on TCE was obtained from a comparison of the estimated increase in cell numbers while growing on TCE and VC obtained by measuring maximum VC utilization rates initially and after utilization of TCE and VC was complete (see Batch Studies under Materials and Methods). The cultures dechlorinated the same chlorine mass during either TCE or VC dechlorination, and at the same rate (FIG. 13). Thus, if growth occurred on TCE, then the increase in cell numbers while growing on TCE should be the same as that while growing on VC. This was found to be the case (Table 5).

TABLE 5

*Dehalococcoides* species strain VS growth yields on TCE and VC
as determined from VC utilization rate measurements, the computed
increase in cell biomass, and the mass dechlorinated.

| | VC | TCE |
|---|---|---|
| Initial VC rate (μmol (d · L)$^{-1}$) | 28 ± 2$^a$ | 28 ± 2$^a$ |
| Initial cells (cell L$^{-1}$)$^b$ | 3.6 ± 0.3$^a$ × 10$^{10}$ | 3.6 ± 0.3$^a$ × 10$^{10}$ |
| Final VC rate (μmol (d · L)$^{-1}$) | 228, 204 | 312, 204 |
| Final cells (cell L$^{-1}$)$^b$ | 2.9 × 10$^{11}$, 2.6 × 10$^{11}$ | 4.0 × 10$^{11}$, 2.6 × 10$^{11}$ |
| Mass dechlorinated (μmol) | 10.39, 10.52 | 10.94, 8.97 |
| Yield (cell μmol$^{-1}$)$^c$ | 4.6 ± 0.3$^a$ × 10$^8$ | 5.8 ± 0.8$^a$ × 10$^8$ |

$^a$Average and range of replicates.
$^b$Determined by dividing VC utilization rate by standardized rate of 7.8 × 10$^{-10}$ μmol ethene/cell · d
$^c$Yield = (20 mL sample/1000 mL)(final cells − initial cells)/mass dechlorinated Thus three separate lines of evidence, one a modeling fit to the data and two others where increase in cell numbers was determined, confirm that growth of strain VS occurred from TCE dehalogenation alone.

The three methods used above all indicate that growth yields with TCE dehalogenation to ethene are similar to that for VC dehalogenation to ethene. If the TCE degradation was co-metabolic, as has been found for the recently isolated, VC-respiring, *Dehalococcoides* isolate BAV1, then the ethene formation rate and the growth yield for the TCE fed cells would be two thirds of that found for the VC fed cells. While such detailed analysis of growth yield through cell counting was not conducted for the KB-1/VC and Pinellas cultures, the maximum growth rates similar determined by the dilution procedure, and their close similarities in TCE utilization to strain VS suggests that they too obtain energy from TCE dehalogenation.

The Pinellas and KB-1/VC cultures failed to dechlorinate PCE. PCE dechlorination did occur after a lag period of 6-12 days with the Victoria mixed culture, suggesting that the presence of an additional dechlorinating microorganism in the culture might be responsible for the eventual PCE dechlorination.

16S rRNA gene sequences. Since the Victoria, KB-1/VC, and Pinellas cultures all exhibited such similar dehalogenation kinetics, a question arises as to whether they all contain the same strain of *Dehalococcoides*. The Victoria culture contains a *Dehalococcoides* strain (Strain VS) which is distinctly different from that in the other two cultures. However, the similarity in 16S rRNA sequence between the Pinellas and KB-1/VC cultures makes it difficult to ascertain if these two cultures contain the same or a different *Dehalococcoides* sp. To ensure no cross contamination occurred during this study, the 16S rRNA gene sequences for the three cultures were obtained, and the numbers of differences in base pairs from that of *Dehalococcoides ethenogenes* strain 195 (GenBank Accession no. AF004928) were determined.

These sequences were 99.4-100% identical with those previously reported for these cultures. The 16S rRNA gene sequences were also determined from cultures taken at the end of the growth experiments to investigate whether contamination between cultures might have occurred during these experiments. All sequences so obtained agreed with those of the starting cultures, thus we conclude that no cross-contamination occurred.

In summary, a dilution procedure was developed that can be used for comparing maximum growth and dehalogenation rates in mixed cultures. This procedure was used to compare three mixed cultures and one pure culture containing *Dehalococcoides*-like microorganisms. *Dehalococcoides*-like bacteria within the three mixed cultures, Victoria, KB-1/VC, and Pinellas, could dehalogenate TCE, DCE, and VC at similar rates, but could not grow on PCE, suggesting they have similar mechanisms for dechlorination. Maximum growth rates for dehalogenating bacteria in the Victoria and KB-1/VC cultures were very similar, and about the same on DCE and VC (0.42 to 0.49 d$^{-1}$), but lower on TCE (0.35 d$^{-1}$). The Pinellas culture had about the same growth rate on DCE (0.43 d$^{-1}$), but lower on VC (0.28 d$^{-1}$) and higher on TCE (0.49 d$^{-1}$). However, the three mixed cultures performed quite differently from *D. ethenogenes* strain 195, which does dechlorinate PCE with growth, but dechlorinates VC only co-metabolically. They also differ from the isolate *Dehalococcoides* isolate BAV1, which grows with VC, but uses TCE only co-metabolically.

The most significant finding of this research is the confirmed ability of the strain VS to obtain energy from each step in the dehalogenation of TCE to ethene. This is an important advantage when using these cultures for bioaugmentation of TCE contaminated sites.

This study also provided additionally evidence for the ability of the model represented by Eq. 4, or its equivalent given elsewhere for the case when electron donor is also limiting, to correctly simulate dehalogenation rates, providing information on the parameters of importance. This equation indicates that the overall growth rate ($\mu$) is equal to the sum of growth rates individually on TCE, DCE, and VC. This may suggest that the maximum growth rate would be greater if growing on all three electron donors rather than on one alone. However, this need not be true because the growth rate is modified by the competitive coefficients, which reduces the growth rate on one electron acceptor when others are present. Thus, in order to obtain correct growth and dehalogenation rates, the complete model with competitive coefficients as provided here is needed.

---

What is claimed is:

1. An isolated nucleic acid encoding a vinyl chloride reductase, wherein the vinyl chloride reductase has the amino acid sequence set forth in SEQ ID NO:2.

2. An isolated nucleic acid encoding a vinyl chloride reductase, wherein said nucleic acid encodes the polypeptide sequences set forth in SEQ ID NO:2 and SEQ ID NO:3.

3. An isolated nucleic acid probe comprising at least 25 contiguous nucleotides of the sequence set forth in SEQ ID NO:1.

4. An isolated nucleic acid probe consisting of at least 25 contiguous nucleotides of the sequence set forth in SEQ ID NO:1.

* * * * *

UNITED STATES PATENT AND TRADEMARK OFFICE
CERTIFICATE OF CORRECTION

PATENT NO. : 8,063,192 B2
APPLICATION NO. : 11/659064
DATED : November 22, 2011
INVENTOR(S) : Alfred M. Spormann Page 1 of 1

It is certified that error appears in the above-identified patent and that said Letters Patent is hereby corrected as shown below:

On the title page, item [75] inventors:

- Replace the word "Nannheim" to read --Mannheim-- in the third to last line.

Signed and Sealed this
Fourth Day of September, 2012

David J. Kappos
*Director of the United States Patent and Trademark Office*